(12) United States Patent
Molaei et al.

(10) Patent No.: US 8,998,973 B2
(45) Date of Patent: Apr. 7, 2015

(54) MEDICAL DEVICES INCLUDING METALLIC FILMS

(75) Inventors: Masoud Molaei, Fremont, CA (US);
Beren W. Correa, Fremont, CA (US);
John Peckham, Sunnyvale, CA (US);
Alexander Leynov, Walnut Creek, CA (US); Stephen Christopher Porter, Oakland, CA (US); Robert Z. Obara, Fremont, CA (US); Delilah Yin Hui, American Canyon, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2565 days.

(21) Appl. No.: 11/025,866

(22) Filed: Dec. 29, 2004

(65) Prior Publication Data

US 2005/0197690 A1    Sep. 8, 2005

Related U.S. Application Data

(60) Provisional application No. 60/549,287, filed on Mar. 2, 2004.

(51) Int. Cl.
| A61F 2/07 | (2013.01) |
| A61F 2/82 | (2013.01) |
| A61F 2/95 | (2013.01) |
| A61F 2/966 | (2013.01) |
| A61F 2/90 | (2013.01) |

(52) U.S. Cl.
CPC ............. *A61F 2/07* (2013.01); *A61F 2002/075* (2013.01); *A61F 2002/9511* (2013.01); *A61F 2002/9665* (2013.01); *A61F 2250/0039* (2013.01); *A61F 2/90* (2013.01); *A61F 2230/0013* (2013.01)

(58) Field of Classification Search
CPC ..... A61F 2/848; A61F 2/07; A61F 2002/075; A61F 2002/9511
USPC ........... 623/1.12, 1.13, 1.15, 1.34, 1.36, 1.16, 623/1.3, 1.31; 606/191, 192, 194, 198
See application file for complete search history.

(56) References Cited

U.S. PATENT DOCUMENTS

| 4,793,348 A | 12/1988 | Palmaz |
| 4,864,824 A | 9/1989 | Gabriel et al. |
| 5,035,706 A * | 7/1991 | Giantureo et al. ............ 606/198 |

(Continued)

FOREIGN PATENT DOCUMENTS

| EP | 0472731 | 8/1991 |
| EP | 0 792 627 A2 | 9/1997 |

(Continued)

OTHER PUBLICATIONS

International Search Report for PCT Application No. PCT/US2005/006993.

(Continued)

*Primary Examiner* — Brian Pellegrino
(74) *Attorney, Agent, or Firm* — Kacvinsky Daisak Bluni PLLC

(57) ABSTRACT

An endoprosthesis for deployment within a body passage includes a framework and a metallic film, which can circumferentially surround the framework or be surrounded by the framework. The framework and metallic film can be attached without using a third material, e.g., without sewing. The framework can define a circumferential recess along at least a portion of its length and circumference. The recess accommodates at least a portion of the metallic film therein.

2 Claims, 16 Drawing Sheets

(56) References Cited

U.S. PATENT DOCUMENTS

| | | | |
|---|---|---|---|
| 5,061,914 A | 10/1991 | Busch et al. | |
| 5,085,535 A | 2/1992 | Solberg et al. | |
| 5,119,555 A | 6/1992 | Johnson | |
| 5,245,738 A | 9/1993 | Johnson | |
| 5,266,073 A * | 11/1993 | Wall | 623/1.2 |
| 5,302,261 A | 4/1994 | LeRoy et al. | |
| 5,306,294 A | 4/1994 | Winston et al. | |
| 5,325,880 A | 7/1994 | Johnson et al. | |
| 5,382,261 A | 1/1995 | Palmaz | |
| 5,405,378 A | 4/1995 | Strecker et al. | |
| 5,441,515 A | 8/1995 | Khosravi et al. | |
| 5,518,680 A | 5/1996 | Cima et al. | |
| 5,554,182 A | 9/1996 | Dinh et al. | |
| 5,556,413 A * | 9/1996 | Lam | 623/1.2 |
| 5,607,466 A | 3/1997 | Imbert et al. | |
| 5,619,177 A | 4/1997 | Johnson et al. | |
| 5,656,036 A | 8/1997 | Palmaz | |
| 5,667,523 A | 9/1997 | Bynon et al. | |
| 5,674,242 A | 10/1997 | Phan et al. | |
| 5,676,697 A * | 10/1997 | McDonald | 623/1.35 |
| 5,728,150 A | 3/1998 | McDonald et al. | |
| 5,755,734 A * | 5/1998 | Richter et al. | 606/194 |
| 5,800,517 A | 9/1998 | Anderson et al. | |
| 5,800,526 A * | 9/1998 | Anderson et al. | 623/1.16 |
| 5,817,102 A * | 10/1998 | Johnson et al. | 606/108 |
| 5,824,042 A * | 10/1998 | Lombardi et al. | 623/1.13 |
| 5,824,049 A | 10/1998 | Ragheb et al. | |
| 5,824,054 A | 10/1998 | Khosravi et al. | |
| RE35,988 E | 12/1998 | Winston et al. | |
| 5,843,158 A * | 12/1998 | Lenker et al. | 623/1.13 |
| 5,843,164 A | 12/1998 | Frantzen et al. | |
| 5,843,289 A | 12/1998 | Lee et al. | |
| 5,849,206 A | 12/1998 | Amon et al. | |
| 5,860,998 A | 1/1999 | Robinson et al. | |
| 5,865,723 A | 2/1999 | Love et al. | |
| 5,882,444 A | 3/1999 | Flomenblit et al. | |
| 5,888,734 A | 3/1999 | Cremer et al. | |
| 5,897,911 A | 4/1999 | Loeffler | |
| 5,903,099 A | 5/1999 | Johnson et al. | |
| 5,938,697 A * | 8/1999 | Killion et al. | 623/1.15 |
| 5,941,249 A | 8/1999 | Maynard | |
| 5,957,929 A | 9/1999 | Brenneman | |
| 5,984,963 A | 11/1999 | Ryan et al. | |
| 6,007,573 A | 12/1999 | Wallace et al. | |
| 6,015,431 A | 1/2000 | Thornton et al. | |
| 6,015,433 A | 1/2000 | Roth | |
| 6,017,977 A | 1/2000 | Evans et al. | |
| 6,036,725 A * | 3/2000 | Avellanet | 623/1.13 |
| 6,043,451 A | 3/2000 | Julien et al. | |
| 6,048,360 A * | 4/2000 | Khosravi et al. | 623/1.11 |
| 6,048,622 A | 4/2000 | Hagood et al. | |
| 6,059,766 A | 5/2000 | Greff | |
| 6,077,298 A | 6/2000 | Tu et al. | |
| 6,096,175 A | 8/2000 | Roth | |
| 6,099,561 A | 8/2000 | Alt | |
| 6,107,004 A | 8/2000 | Donadio, III | |
| 6,120,535 A | 9/2000 | McDonald et al. | |
| 6,132,460 A * | 10/2000 | Thompson | 623/1.15 |
| 6,133,547 A | 10/2000 | Maynard | |
| 6,139,564 A | 10/2000 | Teoh | |
| 6,143,022 A | 11/2000 | Shull et al. | |
| 6,159,239 A | 12/2000 | Greenhalgh | |
| 6,174,330 B1 | 1/2001 | Stinson | |
| 6,190,404 B1 | 2/2001 | Palmaz et al. | |
| 6,206,911 B1 * | 3/2001 | Milo | 623/1.15 |
| 6,224,627 B1 | 5/2001 | Armstrong et al. | |
| 6,224,630 B1 | 5/2001 | Bao et al. | |
| 6,245,104 B1 | 6/2001 | Alt | |
| 6,254,628 B1 | 7/2001 | Wallace et al. | |
| 6,258,117 B1 | 7/2001 | Camrud et al. | |
| 6,290,720 B1 | 9/2001 | Khosravi et al. | |
| 6,303,100 B1 | 10/2001 | Ricci et al. | |
| 6,315,788 B1 | 11/2001 | Roby | |
| 6,315,794 B1 | 11/2001 | Richter | |
| 6,355,055 B1 | 3/2002 | Waksman et al. | |
| 6,379,383 B1 | 4/2002 | Palmaz et al. | |
| 6,398,803 B1 | 6/2002 | Layne et al. | |
| 6,406,487 B2 | 6/2002 | Brenneman | |
| 6,406,490 B1 | 6/2002 | Roth | |
| 6,409,749 B1 | 6/2002 | Maynard | |
| 6,428,569 B1 | 8/2002 | Brown | |
| 6,447,478 B1 | 9/2002 | Maynard | |
| 6,454,738 B1 | 9/2002 | Tran et al. | |
| 6,458,152 B1 | 10/2002 | Khosravi et al. | |
| 6,458,153 B1 | 10/2002 | Bailey et al. | |
| 6,471,980 B2 | 10/2002 | Sirhan et al. | |
| 6,485,510 B1 | 11/2002 | Camrud et al. | |
| 6,506,211 B1 | 1/2003 | Doran et al. | |
| 6,520,984 B1 | 2/2003 | Garrison et al. | |
| 6,527,919 B1 | 3/2003 | Roth | |
| 6,533,905 B2 | 3/2003 | Johnson et al. | |
| 6,537,310 B1 | 3/2003 | Palmaz et al. | |
| 6,558,414 B2 * | 5/2003 | Layne | 623/1.13 |
| 6,605,111 B2 | 8/2003 | Bose et al. | |
| 6,614,570 B2 | 9/2003 | Johnson et al. | |
| 6,618,921 B1 | 9/2003 | Thornton | |
| 6,620,192 B1 | 9/2003 | Jalisi | |
| 6,620,634 B2 | 9/2003 | Johnson et al. | |
| 6,624,730 B2 | 9/2003 | Johnson et al. | |
| 6,629,993 B2 | 10/2003 | Voinov | |
| 6,632,240 B2 | 10/2003 | Khosravi et al. | |
| 6,638,301 B1 | 10/2003 | Chandrasekaran et al. | |
| 6,666,882 B1 | 12/2003 | Bose et al. | |
| 6,669,719 B2 | 12/2003 | Wallace et al. | |
| 6,669,721 B1 | 12/2003 | Bose et al. | |
| 6,669,795 B2 | 12/2003 | Johnson et al. | |
| 6,673,102 B1 | 1/2004 | Vonesh et al. | |
| 6,676,987 B2 | 1/2004 | Zhong et al. | |
| 6,695,865 B2 | 2/2004 | Boyle et al. | |
| 6,699,278 B2 | 3/2004 | Fischell et al. | |
| 6,699,279 B2 | 3/2004 | Stevens et al. | |
| 6,746,478 B2 | 6/2004 | Jayaraman | |
| 6,752,826 B2 | 6/2004 | Holloway et al. | |
| 6,767,418 B1 | 7/2004 | Zhang et al. | |
| 6,776,795 B2 | 8/2004 | Pelton | |
| 6,820,676 B2 | 11/2004 | Palmaz et al. | |
| 6,849,085 B2 | 2/2005 | Marton | |
| 6,936,066 B2 | 8/2005 | Palmaz et al. | |
| 6,953,560 B1 | 10/2005 | Castro et al. | |
| 7,105,018 B1 | 9/2006 | Yip et al. | |
| 7,279,175 B2 | 10/2007 | Chen et al. | |
| 7,410,497 B2 | 8/2008 | Hastings et al. | |
| 7,947,071 B2 | 5/2011 | Schmid et al. | |
| 2001/0001834 A1 | 5/2001 | Palmaz et al. | |
| 2001/0032013 A1 | 10/2001 | Marton | |
| 2001/0039449 A1 | 11/2001 | Johnson et al. | |
| 2001/0044647 A1 * | 11/2001 | Pinchuk et al. | 623/1.31 |
| 2002/0007958 A1 | 1/2002 | Rivelli et al. | |
| 2002/0017503 A1 | 2/2002 | Banas et al. | |
| 2002/0019662 A1 | 2/2002 | Brauckman et al. | |
| 2002/0035774 A1 | 3/2002 | Austin | |
| 2002/0042645 A1 | 4/2002 | Shannon | |
| 2002/0046783 A1 | 4/2002 | Johnson et al. | |
| 2002/0142119 A1 | 10/2002 | Seward et al. | |
| 2002/0151965 A1 | 10/2002 | Roth | |
| 2002/0161342 A1 | 10/2002 | Rivelli, Jr. et al. | |
| 2002/0162605 A1 | 11/2002 | Horton et al. | |
| 2002/0165576 A1 | 11/2002 | Boyle et al. | |
| 2002/0165600 A1 | 11/2002 | Banas et al. | |
| 2002/0173809 A1 | 11/2002 | Fleischman et al. | |
| 2002/0187288 A1 | 12/2002 | Lim et al. | |
| 2002/0193869 A1 | 12/2002 | Dang | |
| 2002/0195579 A1 | 12/2002 | Johnson | |
| 2002/0198584 A1 | 12/2002 | Unsworth et al. | |
| 2003/0002994 A1 | 1/2003 | Johnson et al. | |
| 2003/0004567 A1 | 1/2003 | Boyle et al. | |
| 2003/0018354 A1 | 1/2003 | Roth et al. | |
| 2003/0023303 A1 | 1/2003 | Palmaz et al. | |
| 2003/0040791 A1 | 2/2003 | Oktay | |
| 2003/0050691 A1 | 3/2003 | Shifrin et al. | |
| 2003/0059640 A1 | 3/2003 | Marton et al. | |
| 2003/0060782 A1 | 3/2003 | Bose et al. | |
| 2003/0074049 A1 | 4/2003 | Hoganson et al. | |
| 2003/0078649 A1 | 4/2003 | Camrud et al. | |

(56) References Cited

U.S. PATENT DOCUMENTS

| | | | |
|---|---|---|---|
| 2003/0083731 A1 | 5/2003 | Kramer et al. | |
| 2003/0127318 A1 | 7/2003 | Johnson et al. | |
| 2003/0130718 A1 | 7/2003 | Palmas et al. | |
| 2003/0130721 A1 | 7/2003 | Martin et al. | |
| 2003/0139797 A1 | 7/2003 | Johnson et al. | |
| 2003/0153971 A1 | 8/2003 | Chandrasekaran | |
| 2003/0159920 A1 | 8/2003 | Roth | |
| 2003/0185895 A1 | 10/2003 | Lanphere et al. | |
| 2003/0187495 A1 | 10/2003 | Cully et al. | |
| 2003/0212430 A1 | 11/2003 | Bose et al. | |
| 2004/0006381 A1 | 1/2004 | Sequin et al. | |
| 2004/0014253 A1 | 1/2004 | Gupta et al. | |
| 2004/0030377 A1 | 2/2004 | Dubson et al. | |
| 2004/0034408 A1 | 2/2004 | Majercak et al. | |
| 2004/0054399 A1 | 3/2004 | Roth | |
| 2004/0054406 A1 | 3/2004 | Dubson et al. | |
| 2004/0059410 A1 | 3/2004 | Cox | |
| 2004/0098094 A1* | 5/2004 | Boyle et al. | 623/1.13 |
| 2004/0098095 A1 | 5/2004 | Burnside et al. | |
| 2004/0107004 A1* | 6/2004 | Levine et al. | 623/1.13 |
| 2004/0143317 A1 | 7/2004 | Stinson et al. | |
| 2004/0199239 A1 | 10/2004 | Austin et al. | |
| 2004/0225350 A1 | 11/2004 | Shanley | |
| 2004/0254520 A1 | 12/2004 | Porteous et al. | |
| 2005/0004653 A1 | 1/2005 | Gerberding et al. | |
| 2005/0010275 A1 | 1/2005 | Sahatjian et al. | |
| 2005/0033399 A1 | 2/2005 | Richter | |
| 2005/0165468 A1 | 7/2005 | Marton | |
| 2005/0165469 A1 | 7/2005 | Hogendijk | |
| 2005/0197687 A1 | 9/2005 | Molaei et al. | |
| 2005/0197689 A1 | 9/2005 | Molaei | |
| 2006/0069428 A1 | 3/2006 | Feller | |
| 2006/0100659 A1 | 5/2006 | Dinh et al. | |
| 2006/0115514 A1 | 6/2006 | Gengrinovitch | |
| 2006/0122691 A1 | 6/2006 | Richter | |
| 2006/0142838 A1 | 6/2006 | Molaei et al. | |
| 2006/0142842 A1 | 6/2006 | Molaei et al. | |
| 2006/0142845 A1 | 6/2006 | Molaei et al. | |
| 2006/0142851 A1 | 6/2006 | Molaei et al. | |
| 2006/0147492 A1* | 7/2006 | Hunter et al. | 424/426 |
| 2006/0184231 A1 | 8/2006 | Rucker | |
| 2006/0259131 A1 | 11/2006 | Molaei et al. | |
| 2006/0271158 A1 | 11/2006 | Olson | |
| 2007/0016283 A1 | 1/2007 | Greenhalgh et al. | |
| 2007/0073385 A1 | 3/2007 | Schaeffer et al. | |
| 2007/0112411 A1 | 5/2007 | Obermiller et al. | |
| 2007/0250156 A1 | 10/2007 | Palmaz | |
| 2008/0027388 A1 | 1/2008 | Banas et al. | |
| 2008/0221665 A1 | 9/2008 | Peckham et al. | |
| 2009/0132022 A1 | 5/2009 | Banas | |
| 2009/0187240 A1 | 7/2009 | Clerc et al. | |
| 2010/0030320 A1 | 2/2010 | Feller, III | |
| 2011/0054590 A1 | 3/2011 | Leopold et al. | |

FOREIGN PATENT DOCUMENTS

| | | |
|---|---|---|
| EP | 1 604 697 | 12/2005 |
| GB | 2 125 442 A | 3/1994 |
| JP | 2003-102849 | 8/2003 |
| JP | 2007/502069 | 2/2007 |
| JP | 2007/526098 | 9/2007 |
| JP | 2007/526099 | 9/2007 |
| WO | WO 96/06814 | 3/1996 |
| WO | WO 98/53362 | 11/1998 |
| WO | WO 99/02092 | 1/1999 |
| WO | WO 99/60267 | 12/1999 |
| WO | WO 99/62432 | 12/1999 |
| WO | WO 00/62711 | 10/2000 |
| WO | WO 01/21097 | 3/2001 |
| WO | WO 01/53559 | 7/2001 |
| WO | WO 01/87371 | 11/2001 |
| WO | WO 01/89420 | 11/2001 |
| WO | WO 01/91823 | 12/2001 |
| WO | WO 01/95697 | 12/2001 |
| WO | WO 02/34163 | 5/2002 |
| WO | WO 02/38080 | 5/2002 |
| WO | WO 02/38086 | 5/2002 |
| WO | WO 02/060506 | 8/2002 |
| WO | WO 03/003943 | 1/2003 |
| WO | WO 03/011363 | 2/2003 |
| WO | WO 03/013337 | 2/2003 |
| WO | WO 03/015840 | 2/2003 |
| WO | WO 03/018100 | 3/2003 |
| WO | WO 03/075793 | 9/2003 |
| WO | WO 03/075799 A1 | 9/2003 |
| WO | 03/099161 A2 | 12/2003 |
| WO | WO 2004/002370 A1 | 1/2004 |
| WO | WO 2004/008504 | 1/2004 |
| WO | WO 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | 2006/071245 | 7/2006 |

OTHER PUBLICATIONS

International Search Report for PCT Application No. PCT/US2005/007161.

International Search Report for PCT Application No. PCT/US2005/007173.

International Search Report for PCT Application No. PCT/US2005/006895.

Dieter, George, *Mechanical Metallurgy*, Singapore, McGraw-Hill Book Co., 10$^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "Nitinol Thin Film Three-Dimensional Devices—Fabrication and Applications", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

Neocera, Inc. Brochure—Pulsed Laser Deposition, www.neocera.com [retrieved Dec. 1, 2004].

Pelleiter et al., "Effect of high energy argon implantation into NiTi shape memory alloy", Surface and Coatings Technology, 158-159, 2002, pp. 301-308.

Padhi et al., "Planarization of Copper Thin Films by Electropolishing in Phosphoric Acid for ULSI Application", Journal of Electrochemical Society, vol. 150, 2003, pp. GI0-G14.

Ren et al., "Carbon nitride materials synthesized by Ion-assisted pulsed laser deposition", RIKEN Review No. 43, Jan. 2002, pp. 41-44.

Schetky et al., "Issues in the Further Development of Nitinol Properties and Processing for Medical Device Application", Proceedings, ASM Materials & Processes for Medical Devices Conference, Anaheim, in press, 2003, 6 pages.

(56) References Cited

OTHER PUBLICATIONS

Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.

Stoeckel et al., "A survey of stent designs", Min Invas Ther & Allied Technol, 11(4), 2002, pp. 137-147.

International Search Report for PCT Application No. PCT/US2005/007162.

International Search Report from related International Application No. PCT/US2006/019126 mailed Feb. 1, 2007, 16 pages.

International Search Report and Written Opinion from related PCT application No. PCT/US2005/007282 mailed Jul. 5, 2005, 15 pages.

International Search Report and Written Opinion from related PCT application No. PCT/US2005/007164 mailed Jul. 5, 2005, 13 pages.

International Search Report and Written Opinion from related PCT application No. PCT/US2006/019126 mailed Feb. 1, 2007, 16 pages.

\* cited by examiner

MEDICAL DEVICES INCLUDING METALLIC FILMS

RELATED APPLICATIONS

This application claims the benefit of U.S. provisional patent application No. 60/549,287, filed Mar. 2, 2004, which application is incorporated by reference herein.

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis for deployment within a body passage includes a framework having first and second ends and a tubular member including a metallic film having a thickness of about 50 µm or less and being generally coextensive with at least a portion of the framework. The framework and tubular member can be retained with respect to one another, when deployed in the body passage, at substantially only one distance from the first end of the framework.

The film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties.

When deployed in the body passage, the framework and the tubular member may be secured to one another at one or more different locations, e.g., at a plurality of locations. Each location is spaced a respective distance di from the first end of the framework. A ratio of (a) a maximum difference between distances di to (b) a length of the framework may be about 0.15 or less. Each of the one or more different locations may be located closer to the first end of the framework than to the second end. In embodiments, the framework and tubular member are secured to one another at a single location.

In some embodiments, a delivery device includes the endoprosthesis. The delivery device has a distal end and a proximal portion. The endoprosthesis is in the compressed state and the first end of the framework is located closer to the distal end of the delivery device than to the proximal portion. Prior to deployment in the body passage, the framework and the tubular member may be secured to one another at one or more proximal locations and at one or more other, e.g., distal and/or central, locations. Subsequent to deployment, the framework and tubular member are secured at substantially only one distance from the first end of the framework. For example, one or more filaments securing the other locations may rupture or become undone during deployment.

In some embodiments, an endoprosthesis for deployment within a body passage includes a framework including at least one radial projection having a radially enlarged end and a deposited film generally coextensive with at least a portion of the framework. The film has at least one fenestration and the at least one projection of the framework extends through the fenestration and retains a portion of the deposited film adjacent the fenestration between the radially enlarged end and the framework. The film may be a deposited metallic film including, e.g., deposited nickel and titanium.

The deposited film and framework may have at least some freedom of movement in at least one of a radial, circumferential, or longitudinal dimension.

In some embodiments, an endoprosthesis for deployment within a body passage includes a framework having at least one framework member and a deposited film generally coextensive with at least a portion of the framework. The film includes a first projection having a fixed end and a plurality of free edges. The first projection extends from its fixed end across the framework member to retain the framework and film with respect to one another.

The film may be a deposited metallic film including, e.g., deposited nickel and titanium. The deposited film may have a thickness of about 50 µm or less, 50 µm or less, e.g., about 35 µm or less. The deposited film may have a thickness of 4 µm or greater. The film may exhibit super-elastic properties.

In embodiments, the film includes a second projection having a fixed end and a plurality of free edges. The fixed ends of the first and second projections may be located on opposite sides of the framework member so that the first and second projections extend over the framework member in opposite orientations. A spacing between nearest free edges of the first and second projections may be about equal to or less than a width of the projections.

The endprosthesis and the framework member may have a respective longitudinal axis, with the longitudinal axes may be aligned with one another.

In some embodiments, an endoprosthesis for deployment within a body passage includes a framework defining a perimeter and a deposited film generally coextensive with at least a portion of the framework. The film has a plurality of projections, each projection having a fixed end and a free end. Each projection extends from its fixed end, which may be located on a first side of the perimeter to a free end, which may be located on a second, opposite side of the perimeter to retain the framework and the film with respect to one another.

The film may be a deposited metallic film including, e.g., deposited nickel and titanium. The deposited film may have a thickness of about 50 μm or less, 50 μm or less, e.g., about 35 μm or less. The deposited film may have a thickness of 4 μm or greater. The film may exhibit super-elastic properties.

The projections may extend longitudinally outward from an end of the film.

In some embodiments, an endoprosthesis for deployment within a body passage includes a framework including at least one radial projection and a deposited film generally coextensive with at least a portion of the framework. The film has at least one fenestration through which the at least one projection of the framework extends. A filament extends circumferentially around at least a portion of the film and through the radial projection to retain the framework and tubular member with respect to one another.

The film may be a deposited metallic film including, e.g., deposited nickel and titanium. The deposited film may have a thickness of about 50 μm or less, 50 μm or less, e.g., about 35 μm or less. The deposited film may have a thickness of 4 μm or greater. The film may exhibit super-elastic properties.

In embodiments, an endoprosthesis for deployment within a body passage includes a framework having first and second end portions and a central portion. The central portion and at least the first end portion have a diameter that differs by an amount Δd to form a recess. A tubular member is circumferentially coextensive with at least the central portion of the framework and is at least partially accommodated within the recess.

The central portion may have a smaller diameter than the first end portion so that the recess is formed within an exterior of the framework.

The framework and tubular member may have at least circumferential freedom of movement with respect to one another.

The film may be a deposited metallic film including, e.g., deposited nickel and titanium. The deposited film may have a thickness of about 50 μm or less, 50 μm or less, e.g., about 35 μm or less. The deposited film may have a thickness of 4 μm or greater. The film may exhibit super-elastic properties.

In some embodiments, an endoprosthesis for deployment within a body passage includes a framework and a deposited metal film generally coextensive with the framework, the deposited metal film comprising at least one elongate band and at least one fenestration, the elongate band extending circumferentially with respect to the framework and through the at least one fenestration.

The film may be a deposited metallic film including, e.g., deposited nickel and titanium. The deposited film may have a thickness of about 50 μm or less, 50 μm or less, e.g., about 35 μm or less. The deposited film may have a thickness of 4 μm or greater. The film may exhibit super-elastic properties.

In one aspect, the invention features an endoprosthesis including a metallic film, e.g., a vapor deposited film, including nickel, titanium, and chromium. A ratio of a weight of chromium of the metallic film to a combined weight of nickel, titanium, and chromium of the metallic film is at least 0.001 and can be less than 0.0075.

Other aspects, features, and advantages of the invention will be apparent from the description of the preferred embodiments thereof and from the claims.

BRIEF DESCRIPTION OF THE FIGURES

FIG. 4b is a perspective view of the stent body of the endoprosthesis of FIG. 4a.

FIGS. 5b and 5c show detail of a retention site of the endoprosthesis of FIG. 5a. FIG. 5b being a view from a first side of the tubular member and FIG. 5c being a view from a second, opposing side of the tubular member.

FIG. 6b is a detail view of an end portion of the endoprosthesis of FIG. 6a.

FIG. 8b is a perspective view of the stent body of the endoprosthesis of FIG. 8a.

FIG. 10c is a side view of the tubular member of FIG. 10a.

DETAILED DESCRIPTION

Figure 1:
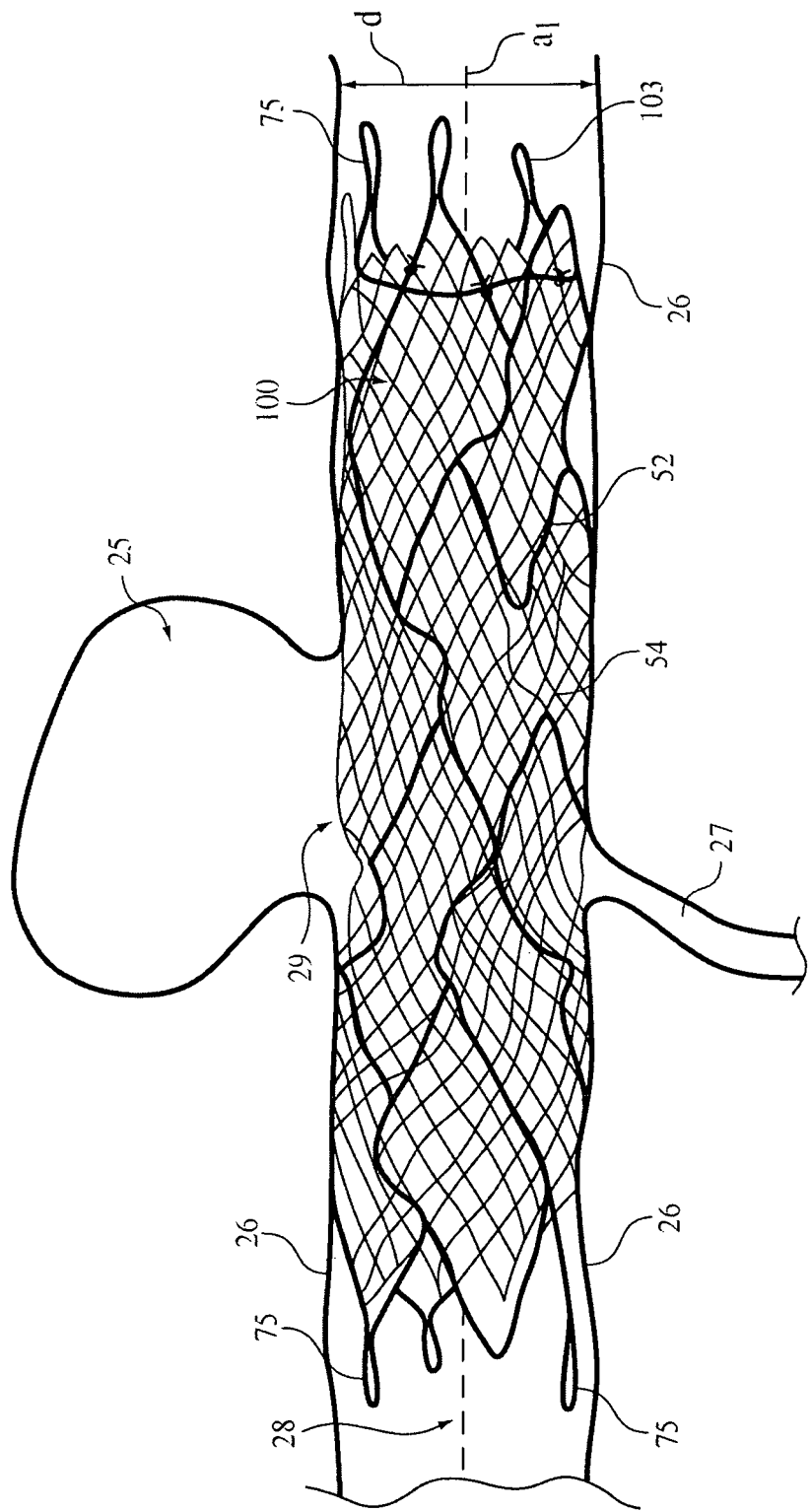
FIG. 1 is a side view of an endoprosthesis in the radially expanded state as deployed within a body passage adjacent an aneurysm.

Referring to FIG. 1, an endoprosthesis 100 is deployed within a body passage, e.g., within a vessel weakened by an aneurysm, e.g., an aneurysm 25 of a vessel 26 of a human brain. Endoprosthesis 100 includes a framework, e.g., a stent body 52, covered by a tubular member or cover 54, made of thin metallic film. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover and occlude the fenestrations of the stent.

In some embodiments, endoprosthesis 100 modifies an amount or velocity of blood passing between vessel 26 and aneurysm 25. For example, prosthesis 100 can be deployed to reduce or block blood flow between vessel 26 and aneurysm 25, e.g., to occlude the aneurysm 25. If so deployed, prosthesis 100 may sufficiently reduce blood flow to allow clotting or other healing processes to take place within aneurysm 25 and/or opening 29 thereof. Tubular member 54 can provide a greater attenuation of the blood flow into the aneurysm 25 than stent body 52 alone. Endoprosthesis 100, however, can allow some flow to pass between vessel 26 and aneurysm 25 even while providing some reduction in the rate and/or volume of flow. Prosthesis 100 can also (or alternatively) allow blood to pass between vessel 26 containing the prosthesis and adjacent vessels, e.g., feeder vessel 27, while still providing reduced flow with respect to the aneurysm.

Figure 2A:
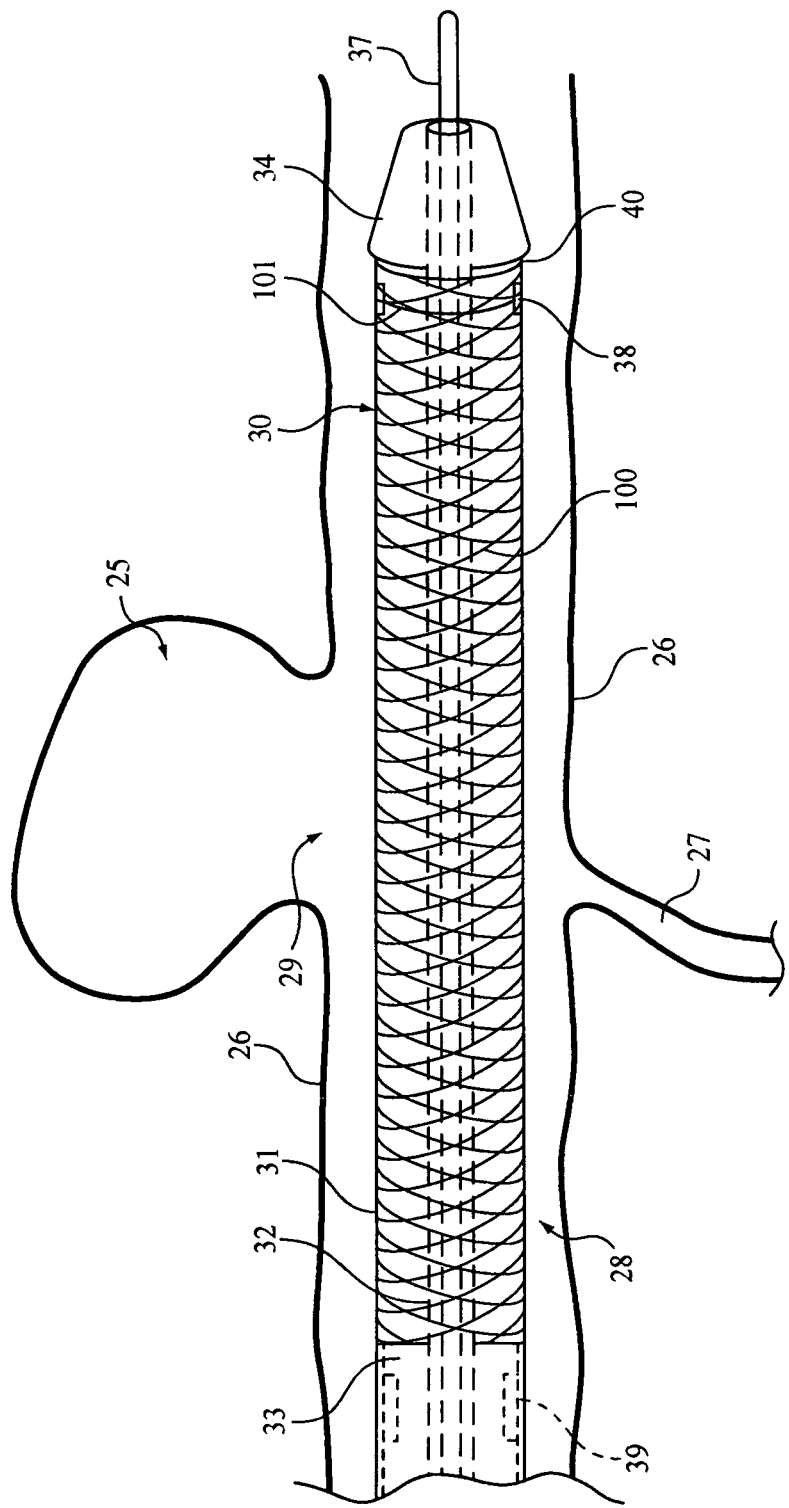
FIG. 2a is a side view of a distal portion of a deployment device prior to radial expansion of the endoprosthesis.

Referring to FIG. 2a, endoprosthesis 100 is deployed to aneurysm 25 using a deployment device 30, which includes a retractable outer sheath 31 and an inner catheter 32. FIG. 2a shows only a distal portion of the delivery device. An operator manipulates the device 30 using a proximal portion (not shown). Device 30 is introduced over a guide wire 37 extending along the interior 28 of vessel 26. During introduction, the endoprosthesis 100 is radially compacted between outer sheath 31 and inner catheter 32 adjacent a distal end 40 of the outer sheath. Endoprosthesis 100 is longitudinally restrained by a proximal stop 33 and a distal tip 34 of inner catheter 32. Device 30 includes distal and proximal markers 38,39, which can be radiographically monitored to determine when endoprosthesis 100 has reached aneurysm 25. Prosthesis 100 includes markers 75, to provide radiopacity, which can also or alternatively be used to visualize the position of endoprosthesis 100.

Figure 2B:
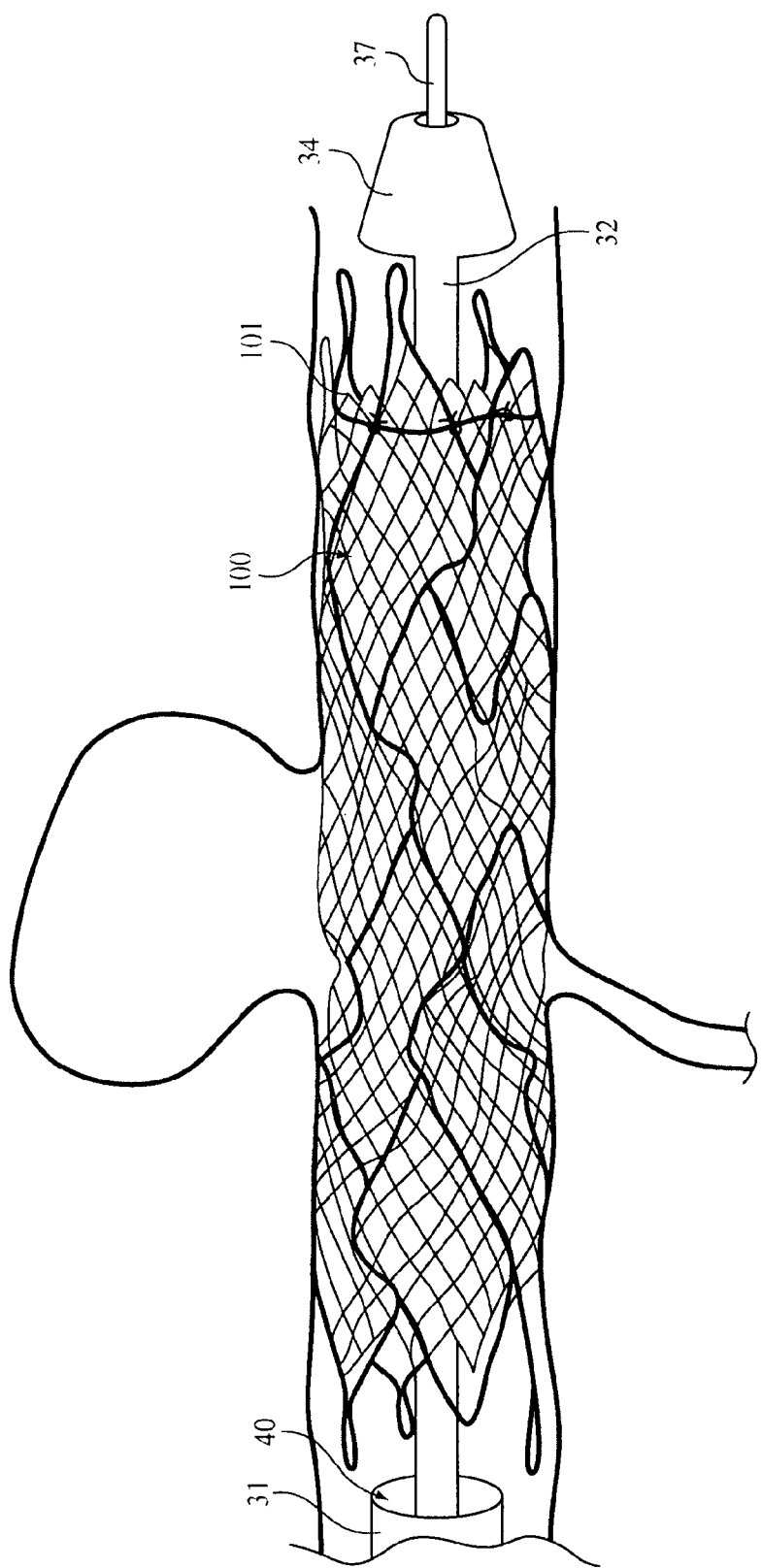
FIG. 2b is a side view of the distal portion of the deployment device subsequent to radial expansion of the endoprosthesis adjacent the aneurysm.

With reference to FIG. 2b, the outer sheath 31 is retracted upon reaching the desired deployment site, e.g., aneurysm 25. In some embodiments, endoprosthesis 100 self-expands by its own internal elastic restoring force when the radially restraining outer sheath is retracted. Alternatively, or in combination with self-expansion, deployment of prosthesis 100 may include use of a balloon or other device to radially expand prosthesis 100 within vessel 26. The inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

Upon expansion, endoprosthesis 100 assumes a shape and radial extent generally coextensive with an inner surface of the vessel 26, e.g., a tubular shape centered about a longitudinal axis $a_1$ of the prosthesis (FIG. 1). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis $a_1$ of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

In some embodiments the tubular member 54 of endprosthesis 100 includes a metallic film deposited by a vapor deposition process. Vapor deposited materials are formed by depositing film constituents from a vapor or a vacuum onto a surface. In embodiments, the constituents are vaporized by bombarding, heating or sputtering a bulk target. The vaporized constituents deposit on a substrate to form the film. Deposited films can exhibit highly uniform thickness and microstructure in very thin films, e.g. about 50 microns or less, e.g. 4-35 microns. Suitable vapor deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In some embodiments, the deposited film can include an alloy of nickel and titanium present in amounts sufficient to provide the deposited film with desirable mechanical or shape memory properties. For example, the film may include an alloy, e.g., a superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003. The alloy may be nitinol. The alloy may include a third compound, e.g., chromium, which modifies a mechanical property, e.g., a stiffness or elasticity, of the film. Tubular member 54 may include a deposited metal film including nickel, titanium, and, optionally, chromium. Exemplary films and deposition of such films is described in U.S. patent application Ser. No. 11/025,860, filed Dec. 29, 2004, titled MEDICAL DEVICES INCLUDING METALLIC FILMS AND METHODS FOR MAKING SAME, which application is incorporated herein by reference.

Figure 3A:
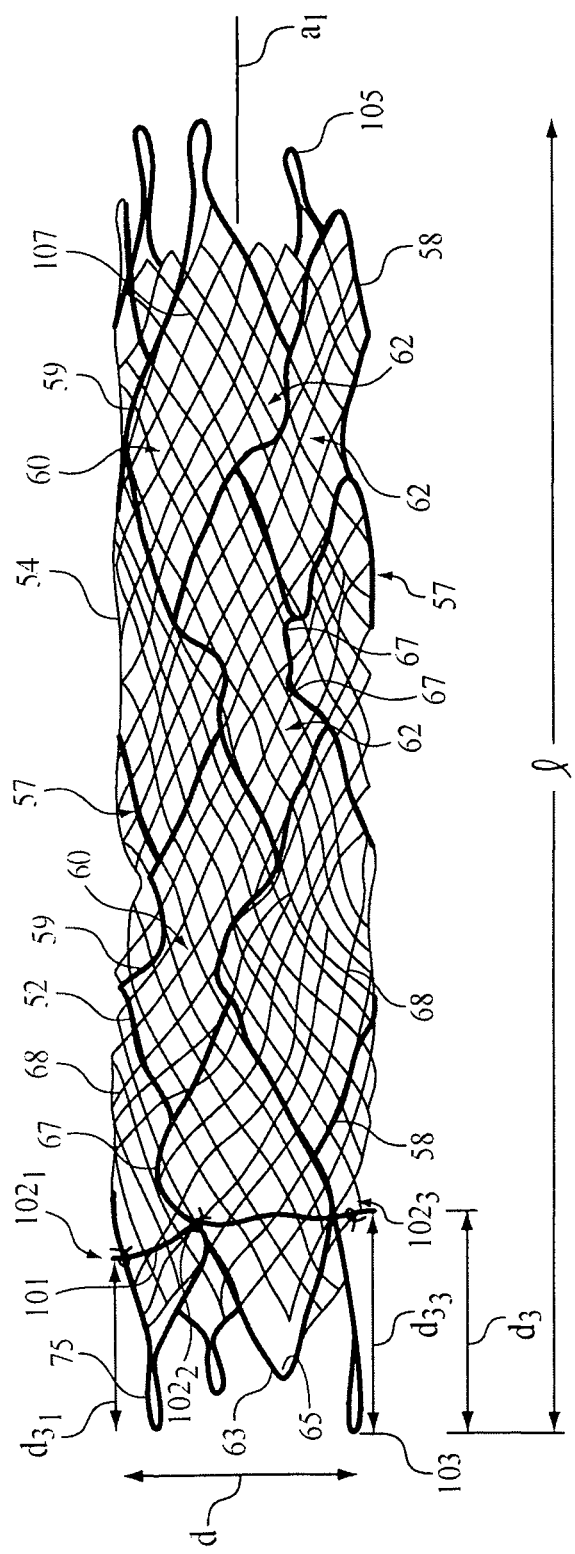
FIG. 3a is a side view of the endoprosthesis of FIG. 1 removed from the body passage and viewed from the opposite side.

Referring to FIG. 3a, endoprosthesis 100 includes stent body 52 and tubular member 54, which are secured together by a filament 101 at substantially only one location relative to a length l of the prosthesis. Stent body 54 includes a plurality of framework members. A plurality of circumferential bands 57 are defined by longitudinal members 58. Adjacent circumferential bands are connected by connectors 59 and define fenestrations 60 therebetween.

Tubular member 54 is defined by a plurality of longitudinal members 68, which themselves define fenestrations 62 therebetween.

Filament 101, which, like all filaments discussed herein can be formed of a polymer, a suture, a ductile metal wire, such as nitinol or gold wire, or other material, at least partially encircles prosthesis 100 securing stent body 52 and tubular member 54 at each of a plurality of retention sites $102_i$, where, i is at least 1 and may be 2 or more, 3 or more, 4 or more, e.g., 6 or more. At each site 102, filament 101 may be threaded through adjacent fenestrations 62 of tubular member 54 and at least partially around a longitudinal member 58 or a connector 59 of stent body 52. Each filament may connect at least two sites 102, e.g., at least 3 sites.

Each of the retention sites 102 can be located at substantially the same distance from a distal or proximal end of prosthesis 100. In the embodiment shown, each site $102i$ is located at a respective distance $d3i$ from a distal end 103 of prosthesis 100. Taken together, sites 102 are located an average distance $d_3$ from the distal end 103 of prosthesis 100. A ratio of average distance $d_3$ to the total length l of prosthesis 100 may be 50% or less, 35% or less, 25% or less, 15% or less, or 5% or less. A maximum difference in the distance $d_{3i}$ for different retention sites $102_i$ relative to length l may be 15% or less, 5% or less, or 2.5% or less. In some embodiments, retention sites $102_i$ are at substantially the same distance, e.g., the same distance, from an end of prosthesis 100. Retention sites 102 may be located with respect to a proximal end 105 of prosthesis 100 in the same manner as that described with respect to distal end 103. Retention sites 102 may be located centrally with respect to ends 103,105.

Because stent body 52 and tubular member 54 are secured together closer to distal end 103 than to proximal end 105, more proximal portions of stent body 52 and tubular member 54 may move with respect to one another, e.g., longitudinally along longitudinal axis $a_2$ or circumferentially with respect to prosthesis 100. Thus, during radial expansion, e.g., during deployment in a body passage, or radial compression, e.g., when loading the prosthesis within a delivery device, differential length changes between stent body 52 and tubular member 54 have little or no tendency to create tension or compression between portions secured at different locations along longitudinal axis $a_1$. Accordingly, upon radial compression and expansion, stent body 52 and tubular member 54 may tolerate a substantial length change differential, e.g., the length change differential may be 15% or more, 25% or more, or 35% or more. In some embodiments, the length change differential is 20% or less, 15% or less, 10% or less, or 5% or less.

The longitudinal length change exhibited by tubular member 54 upon expansion and compression can be related to the shape and size of fenestrations present along the member. In general, greater longitudinal contraction upon radial expansion occurs as the circumferential dimension of the fenestrations increases. Accordingly, the shape and size of the fenestrations may be modified to reduce or increase the longitudinal length change in relation to a stent body.

In some embodiments, retention sites 102 are positioned to selectively facilitate radial compression or radial expansion of the prosthesis. For example, deployment and radial expansion of prosthesis 100 may include withdrawing a sheath that circumferentially surrounds a radially compressed prosthesis 100. The withdrawing sheath generally moves from distal portions of prosthesis 100 toward more proximal portions. In the embodiment shown (FIG. 3a) with retention sites 102 near the distal end of the prosthesis, friction between the sheath and stent body 52 or tubular member 54 has little or no tendency to create compression between proximally secured portions secured at different locations along longitudinal axis $a_1$ because there are no proximal retention sites. In embodiments including proximal retention sites as opposed to distal retention sites, the prosthesis behaves similarly during loading, which may include passing a sheath over the prosthesis from the proximal end toward the distal end.

In some embodiments, the tubular member and stent body are secured together at both ends prior to loading into a delivery device. The retention at a first end, e.g., the distal end, is configured to remain intact during loading and deployment. The retention at a second end, e.g., the proximal end, can be removed after loading or does not remain intact during delivery and radial expansion. For example, the proximal end of the stent body and tubular member can be secured using a filament that is removable after loading. The removable retention assists the loading process as described above and, upon its removal, allows the prosthesis to accommodate length changes and sheath withdrawal during implantation. Accordingly, a method for loading a delivery device for deploying an endoprosthesis can include loading the endoprosthesis into the delivery device with a stent body and tubular member of the endoprosthesis being initially secured at both distal and proximal ends thereof. As part of or after a process for radially compressing the endoprosthesis, retention sites at one end, e.g., the proximal end, are removed (or simply do not survive the complete loading process).

Filament 101 is shown in FIG. 3a as passing generally around the exterior of tubular member 54. In other embodiments, one or more portions of filament 101 may pass inside of tubular member 54.

In some embodiments, filament 101 only partially encircles the endoprosthesis. An endoprosthesis may include a plurality of such partially-encircling filaments. In some embodiments, the filaments radially constrict tubular member 54 such that the tubular member is compressed between the filaments and stent body. In other embodiments, the filaments exert little or no radially constrictive force. Such filaments may nonetheless operate to prevent tubular member 54 and stent body 52 from becoming displaced along the longitudinal axis of the prosthesis.

In some embodiments, the tubular member differs from a fabric at least in that the tubular member lacks fibers than can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process.

Figure 3B:
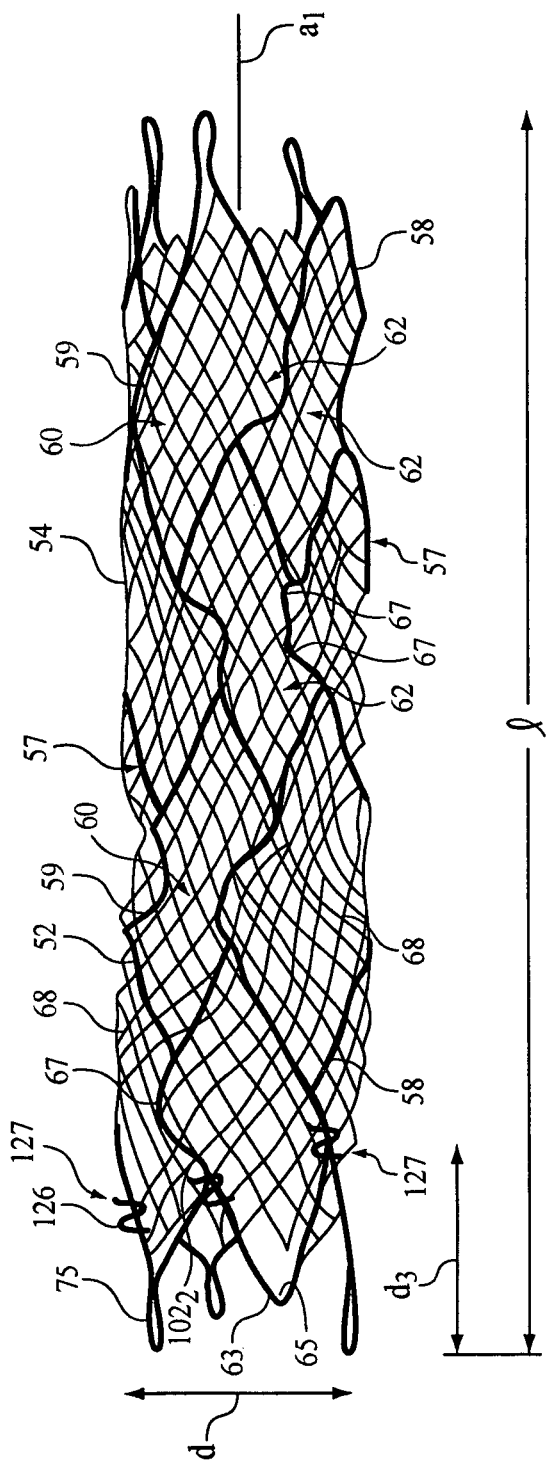
FIG. 3b is a side view of an embodiment of an endoprosthesis including a stent body and a tubular member.

Referring to FIG. 3b, an endoprosthesis 125 includes stent body 52 and tubular member 54, which are secured together by filaments 126 at substantially only one location along a length l of the prosthesis. Each filament 126 secures stent body 52 and tubular member 54 at only a single retention site 127. For example, at each location 127, filament 126 may be threaded through adjacent fenestrations 62 of tubular member 54 and at least partially around a longitudinal member 58 or connector 59 of stent body 52 without then extending to an adjacent retention site 127.

Retention sites 127 may be located and positioned with respect to longitudinal axis a1, length l, and distance $d_3$ of prosthesis 125, as retention sites 102 are located and positioned with respect to longitudinal axis a1, length l, and distance $d_3$ of prosthesis 100.

Figure 3C:
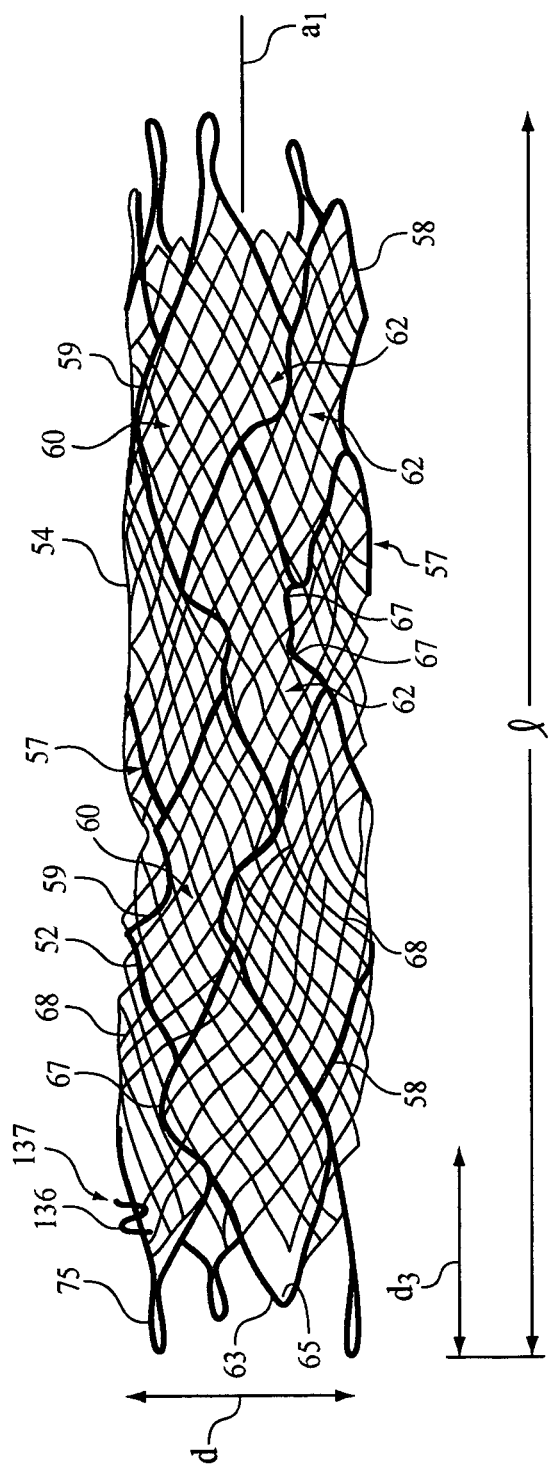
FIG. 3c is a side view of an embodiment of an endoprosthesis including a stent body and a tubular member.

Referring to FIG. 3c, an endoprosthesis 135 includes stent body 52 and tubular member 54, which are secured together by a filament 136 at substantially only one location with respect to a length l of the prosthesis. Filament 136 secures stent body 52 and tubular member 54 at only a single retention site 137. For example, at site 137, filament 136 may be threaded through adjacent fenestrations 62 of tubular member 54 and at least partially around a longitudinal member 58 or connector 59 of stent body 52. Filament 136 may, but in the embodiment shown does not, extend to an adjacent of longitudinal member 58 or connector 59.

Retention site 137 may be located and positioned with respect to longitudinal axis a1, length l, and distance $d_3$ of prosthesis 135, as retention sites 102 are located and positioned with respect to longitudinal axis a1, length l, and distance $d_3$ of prosthesis 100. For example, the single retention site 137 may be located distally, proximally, or centrally with respect to prosthesis 135. Retention site 137 may be a single point along prosthesis 135.

Figure 3D:
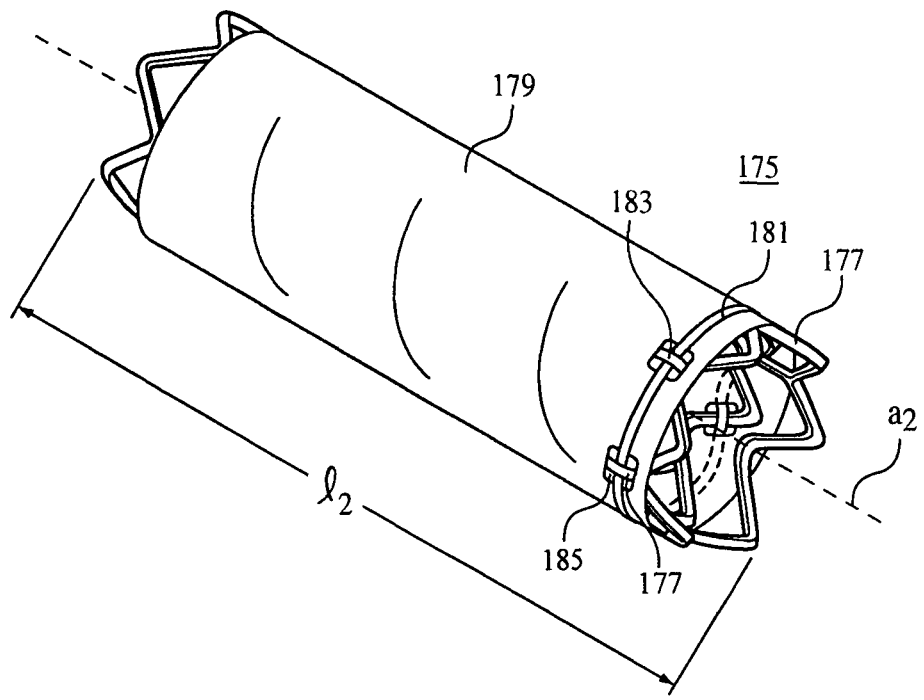
FIG. 3d is a perspective view of an embodiment of an endoprosthesis including a stent body and a tubular member.

Referring to FIG. 3d, an endoprosthesis 175 includes a stent body 177 and a tubular member 179, which are secured together by a filament 181 at substantially only one location with respect to a length l2 of the prosthesis 175. Filament 181 at least partially encircles prosthesis, passing through retention fenestrations 185 of tubular member 179 and at least partially around longitudinal members 183 of stent body 177.

Figure 3E:
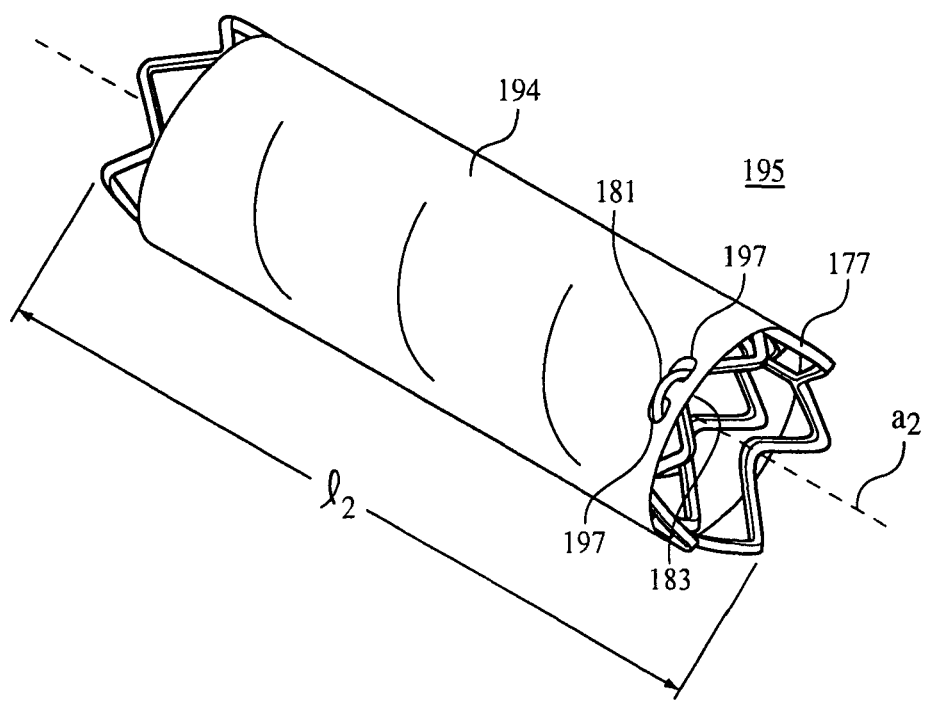
FIG. 3e is a perspective view of an embodiment of an endoprosthesis including a stent body and a tubular member.

Referring to FIG. 3e, an endoprosthesis 195 includes stent body 177 and a tubular member 194, which are secured together by a filament 181 at substantially only one location with respect to length l2 of the prosthesis 195. Filament 181 does not encircle prosthesis. Rather, filament 181 passes through adjacent retention fenestrations 197 of tubular member 194 and at least partially around a longitudinal member 183 of stent body 177 so as to define a single retention site. In some embodiments, filament 181 allows some relative radial and or longitudinal freedom of movement between stent body 52 and tubular member 54. In some embodiments, filament 181 allows essentially no relative radial and or longitudinal freedom of movement between stent body 52 and tubular member 54.

In some embodiments, a tubular member includes a plurality of fenestrations configured to modify a flow of blood between a vessel and aneurysm as discussed above. The tubular member and a stent body can be secured to one another by filaments that extend through fenestrations having a size and shape identical to fenestrations that modify the flow of blood. In other embodiments, tubular member fenestration are particularly associated with retention of the tubular member with respect to the stent body. For example, the size and location of such fenestrations may correspond with certain sites of the stent body. The only fenestrations of the tubular member may be associated with retention of the tubular member and stent body.

Figure 4A:
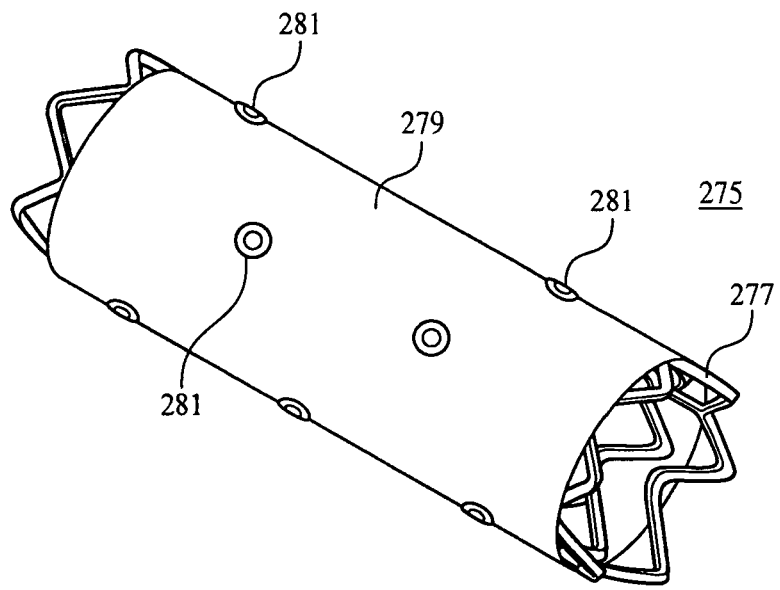
FIG. 4a is a perspective view of an embodiment of an endoprosthesis including a stent body and a tubular member.
Figure 4B:
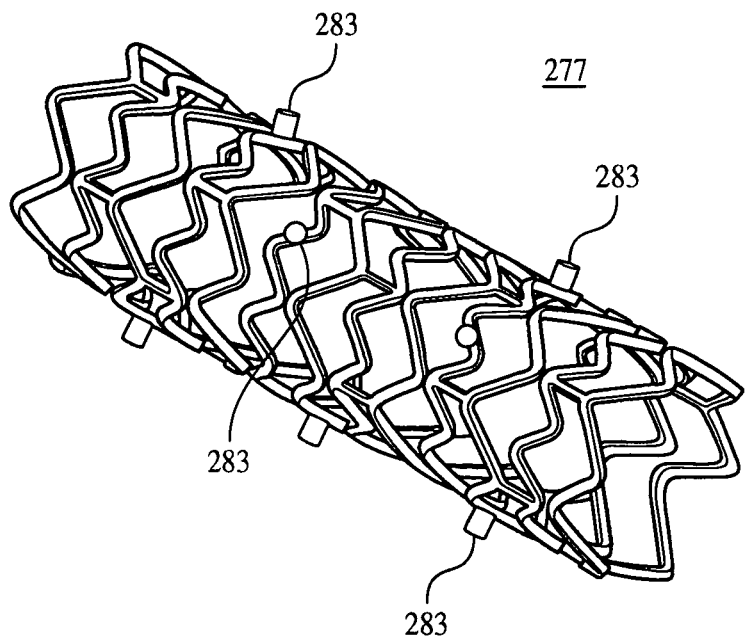

Referring to FIGS. 4a and 4b, an endoprosthesis 275 includes a stent body 277 and a tubular member 279, which can be secured together with complementary elements that are integral with the stent body and tubular member. For example, the stent body 277 and tubular member 279 can be secured together without a third material or structure. In the embodiment shown, stent body 277 includes a plurality of projections, e.g., pins 283 that extend generally radially, e.g., radially outward or inward, from the stent body. Tubular member 279 includes a plurality of fenestrations that align with pins 283. Upon positioning tubular member 279 circumferentially with respect to stent body 277, the pins 283 extend through the fenestrations. Pins 283 are then radially enlarged, as by compression along their length, to form a cap or grommet-like structure. The radially enlarged pins 283 can obscure fenestrations of the tubular member 279 as shown.

Each radially enlarged pin forms a retention site 281 at which a portion of tubular member 279 adjacent the fenestration is retained between, e.g., compressed between, stent body 277 and the cap or grommet-like structure of the radially enlarged pin. The retention is sufficient to limit or prevent the complete separation of the tubular member and stent body (in the absence of damage to either one). In some embodiments, the size and shape of the fenestrations and the amount of compression along the length of each pin is configured to allow the tubular member and stent body radial, circumferential, and/or longitudinal freedom of movement with respect to one another. For example, the radial, circumferential, and/or longitudinal freedom of movement may be at least 2.5%, at least 5%, at least 10%, at least 20% relative to the radius, circumference, or length of the endoprosthesis, respectively. In such embodiments, fenestrations of the tubular member 279 may be shaped to allow the movement. For example, a circumferentially extending slot allows circumferential movement between the stent body and tubular member. In some embodiments, no such freedom of movement is allowed in one or more dimensions.

In some embodiments, the endoprosthesis includes only one retention site 281, which may be located near an end of the prosthesis or a middle. A plurality of retention sites 281 may be positioned at various locations along a longitudinal axis of prosthesis 275. Alternatively, a plurality of retention sites 281 may be located at substantially one distance with respect to a proximal or distal end of the prosthesis, e.g., as discussed with respect to prosthesis 100.

In some embodiments, pins 283 have a different strength or a different malleability than other portions of stent body 277. For example, pins 283 may be formed with a different composition and/or microstructure to provide pins 283 with more malleability than circumferential bands 287, which contribute to radial expansion of prosthesis 277.

Figure 5A:
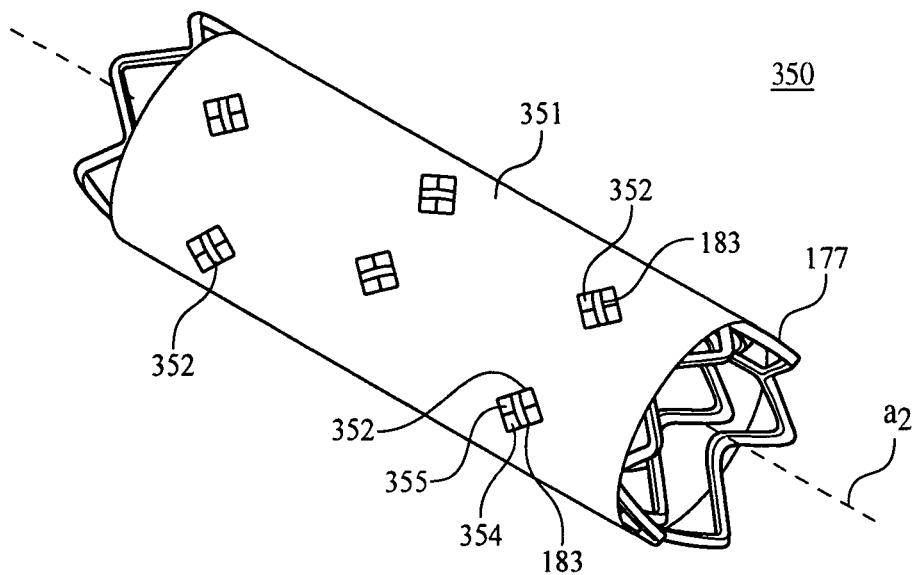
FIG. 5a is a perspective view of an embodiment of an endoprosthesis including a stent body and a tubular member.
Figure 5B:
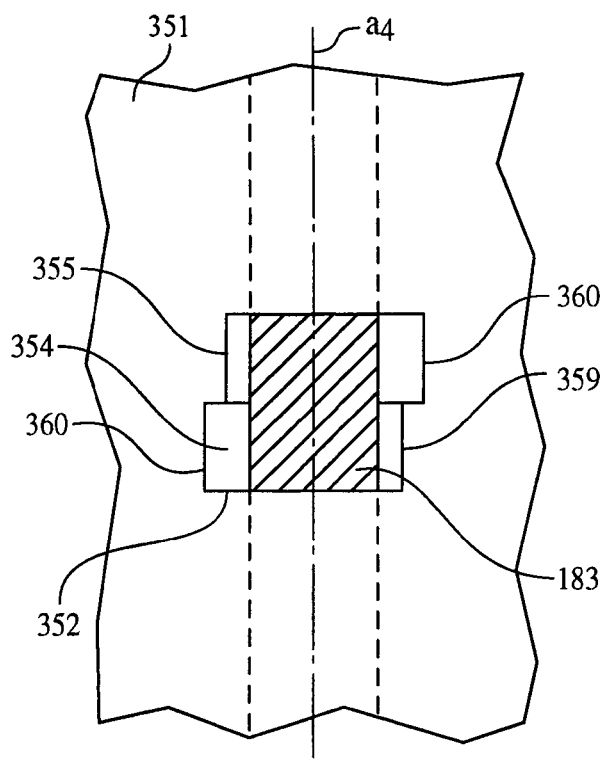
Figure 5C:
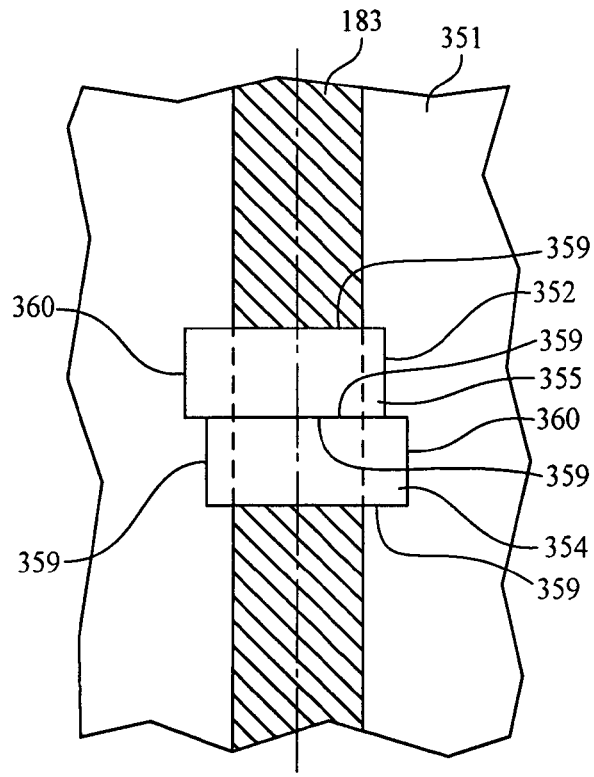

Referring to FIG. 5a, an endoprosthesis 350 includes a stent body 177 and a tubular member 351 which can be secured together with complementary elements that are integral with the stent body and tubular member. Stent body 177 and tubular member 351 are secured to one another by at least one retention site 352. Referring also to FIGS. 5b and 5c, each retention site includes a first tab 354 and an optional second tab 355. Each tab may have one or more free edges 359 and at least one fixed end or edge 360, which is joined with tubular member 351. The nearest free edges of tabs 354,355, which edges are adjacent in the embodiment shown, may, in other embodiments, be separated by a distance about equal to or less than a width of each tab, e.g., a width of each fixed edge.

Each tab 354,355 extends over, e.g., is hooked over, a longitudinal member 183 of stent body 177. Each tab may extend from its fixed end, which is generally located on a first side of a local circumferential perimeter of the stent body to the opposite side of the perimeter. For example, fixed ends 360 of tabs 355 are located outside the local perimeter of stent body 177. The tabs 355 extend from the fixed ends 360 toward the inside of the perimeter.

Each tab may exert a force urging the tab toward tubular member 351, e.g., out of the page in FIG. 5b. For example, tabs 354,355 formed of a memory alloy such as nitinol may be shape set in an orientation that enhances such force. Hence, longitudinal member 183 may be compressed between the tabs 354,355 and tubular member 351.

If more than one retention site is present, the retention sites may be located at different distances from a distal or proximal end of prosthesis 350 as shown. Alternatively, a plurality of retention sites may be located at substantially the same distance with respect to a distal or proximal end of prosthesis 350 as discussed for prostheses 100, 125, and 135.

Stent body 177 and tubular member 351 may have freedom of movement with respect to one another along a longitudinal axis a3 of prosthesis 351 and/or circumferentially with respect to prosthesis 351. For example, in some embodiments, most or all of tabs 354,355 engage only longitudinal members having a longitudinal axis a4 that is aligned with axis a3 of the prosthesis. Such a construction can allow for longitudinal freedom of movement. In other embodiments, most or all of tabs 354,355 engage only longitudinal members having a longitudinal axis a4 that is at a non-zero angle with respect to axis a3 of prosthesis 325, e.g., at 45° thereto or perpendicular thereto. Such a construction can allow for circumferential freedom of movement.

In some embodiments, tabs 354,355 are unitary with tubular member 351. For example, tabs 354,355 may be formed by laser cutting tublar member 351 along dimensions defining free edges 359 of the resulting tabs. In other embodiments, tabs 354,355 are formed by securing another piece of material adjacent to a fenestration of tubular member 351. In any event, whether or not tubular member 351 includes a deposited film, tabs 354,355 may be made of a metal, e.g., a memory alloy such as nitinol. Tabs 354,355 may include a memory alloy of titanium, nickel, and, optionally, chromium.

In some embodiments, tabs 345,355 are subjected to a process that modifies, e.g., increases a number of dislocations.

Tubular member 351 is shown as surrounding stent body 177. In other embodiments, a portion or all of tubular member 351 is disposed within a circumference of stent body 177. Tubular member 351 is shown as lacking fenestrations except for those associated with retention sites 352. In other embodiments, tubular member 351 may include a plurality of fenestrations not associated with retention sites, e.g., as discussed with respect to tubular member 54.

Figure 6A:
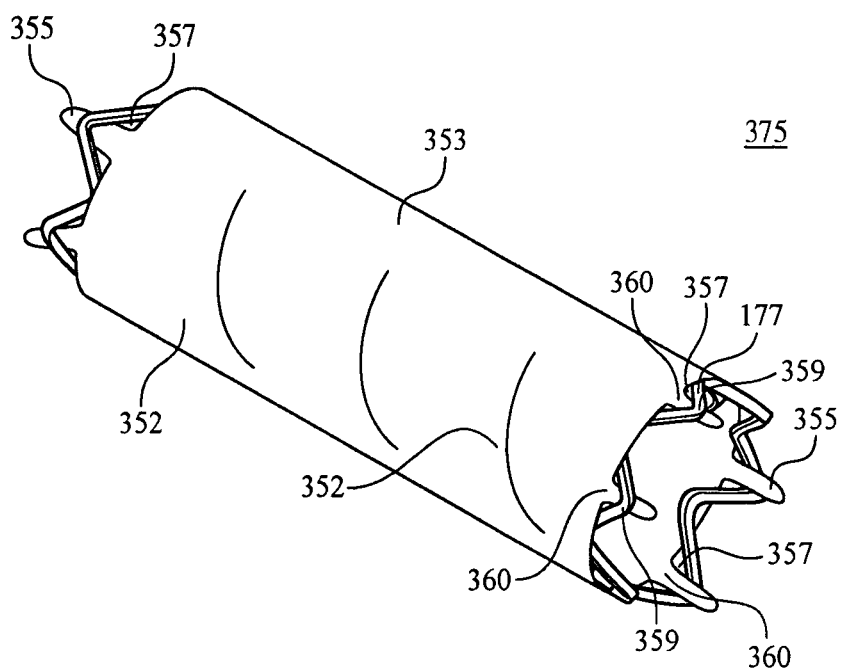
FIG. 6a is a perspective view of an embodiment of an endoprosthesis including a stent body and a tubular member.
Figure 6B:
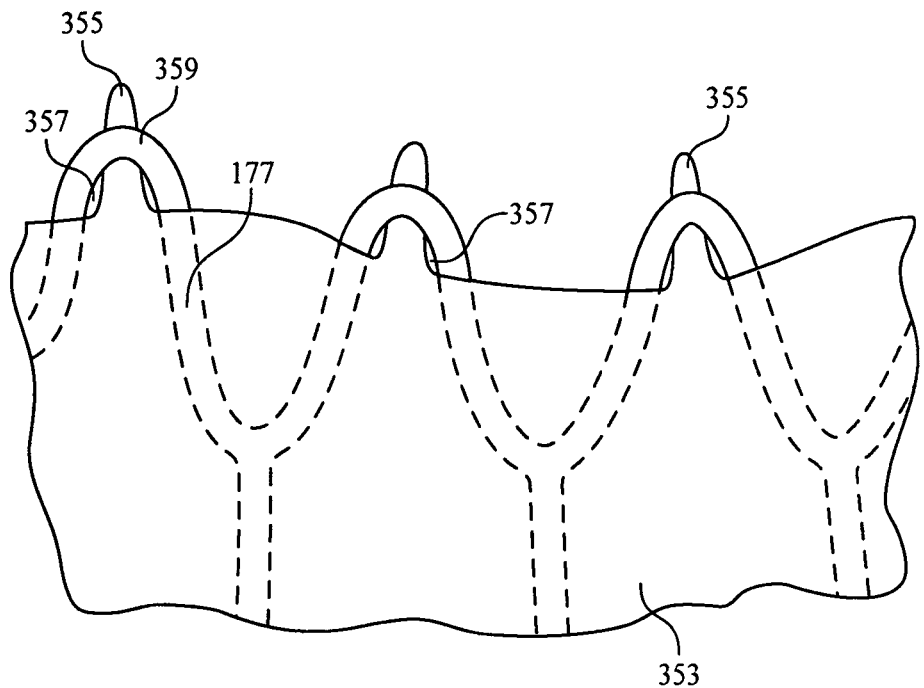

Referring to FIGS. 6a and 6b, an endoprosthesis 375 includes a stent body 177 and a tubular member 353, which can be secured together with complementary elements that are integral with the stent body and tubular member. In particular, tabs 355 of tubular member 353 engage fenestrations 357 of stent body 177. Engagement between the tabs 355 and fenestrations 177 retains the tubular member 353 and stent body with respect to one another. Tabs 355 can be folded back on themselves about portion 359 of stent body 177.

In some embodiments, tabs 355 are unitary with tubular member 353. For example, tabs 355 can be deposited as a portion of a metallic film of the tubular member. Alternatively, tabs 355 can be machined, e.g., by laser cutting, to form tubular member 353. In other embodiments, tabs 355 include a separate piece of material that is attached to the bulk of tubular member 353. Such attachment may be provided using, e.g., mechanical, brazing, welding, or adhesive retention.

In the embodiment shown in FIG. 6a, tubular member 353 surrounds stent body 177. Each tab 355 extends radially inward of a terminus 359 of stent body 355. Tabs 355 may be formed with a force that urges the tabs radially outward, e.g., out of the page with respect to FIG. 6b, so as to more securely engage stent body 177. For example, tabs 355 may be formed of a memory alloy that is shape set to a radially outwardly projecting state.

Figure 6C:
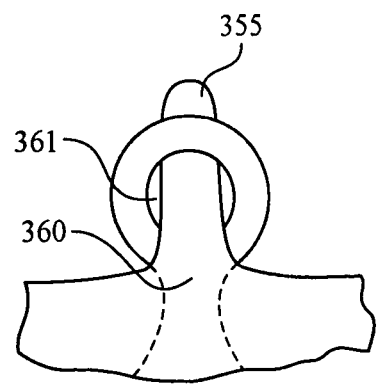
FIGS. 6c and 6d are detail views of alternative retention sites between a tubular member and a stent body.

Referring to FIG. 6c, another embodiment of an engagement between tab 355 and an eyelet 361 of a stent body (the major portion of which is not shown) includes tab 355 extending through a hole 363 having a maximum inner extent of about 5 times or less of a width of tab 355, e.g., about 2.5 times or less of a width of tab 355.

Figure 6D:
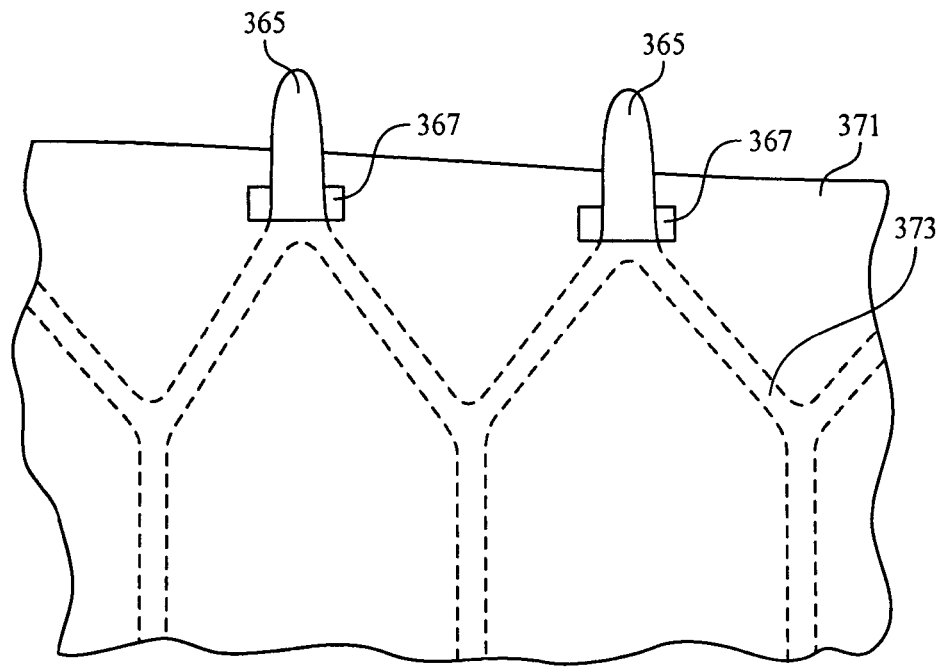

Referring to FIG. 6d, in another embodiment, a tubular member 371 includes one or more fenestrations 367. Stent body 373 includes one or more projections or tabs 365, which engage a respective fenestration 367 of the tubular member. Tabs 365 may include radiopaque markers. The engagement can secure the stent body and tubular member together without use of a third material to form an endoprosthesis. In some embodiments, one or more fenestrations 367 and tabs 365 are located at one end only of the endoprosthesis. In other embodiments, one or more fenestrations 367 and tabs 365 are located at both ends of the endoprosthesis.

Tubular member 371 may surround stent body 373 or be surrounded by the stent body. In any event, either or both tubular member and stent body may be provided with a radial force that enhances the retention between the tubular member and stent body. For example, in embodiments in which tubular member 371 surrounds stent body 373, end portions of tubular member 371 may exert a radial inward force against tabs 365 of stent body 373.

In some embodiments, prosthesis 350 includes only a single tab engaging a single fenestration of the stent body. In other embodiments, a plurality of circumferentially located tabs engage a respective fenestration at one end only of the prosthesis, e.g., only the proximal or distal end.

Tabs of endoprostheses shown in FIGS. 6a-6d are depicted as extending away from a longitudinal center of the prosthesis, e.g., tabs 355 have an end fixed with respect to tubular member 353 and an end free with respect to tubular member 353, wherein the fixed end is positioned closer to the longitudinal center of the prosthesis. In other embodiments, such tabs may extend inward toward the center. For example, the fixed end of one or more tabs 355 can be located closer than the free end of the one or more tabs to the ends of the endoprosthesis so that the tabs extend toward the longitudinal center of the endprosthesis. In other embodiments, the tabs are oriented along a dimension that extends both circumferentially and longitudinally with respect to the endoprosthesis. In such embodiments, the stent body and tubular member may be allowed some degree of rotational and longitudinal freedom of movement.

Figure 7B:
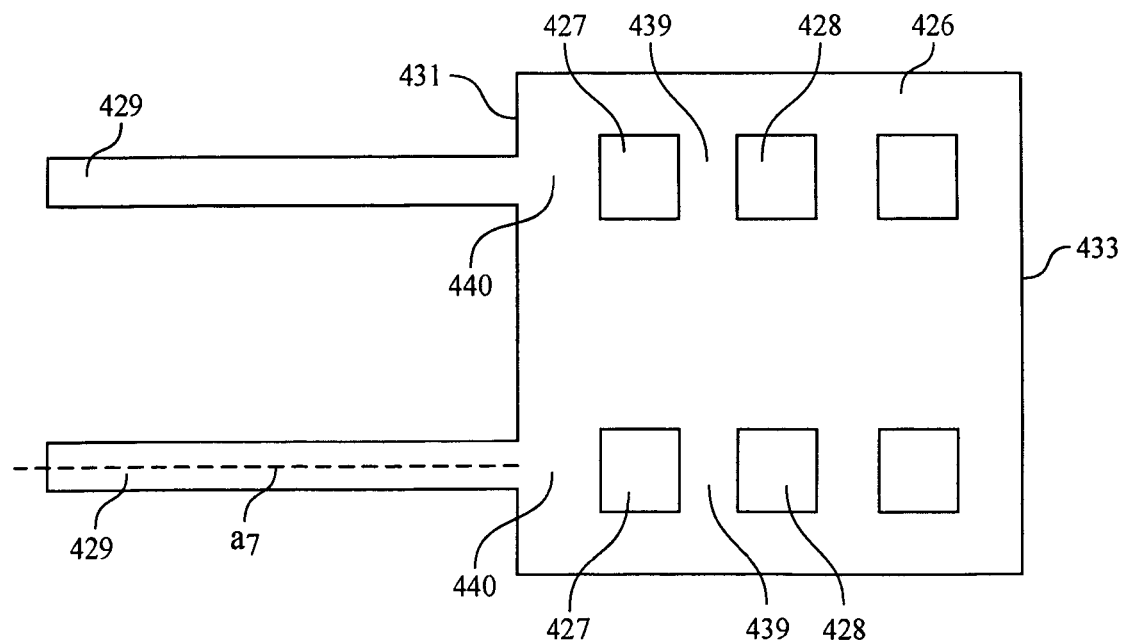
FIG. 7b is a top view of the tubular member of the endoprosthesis of FIG. 7a. The tubular member is shown in two dimensions.
Figure 7A:
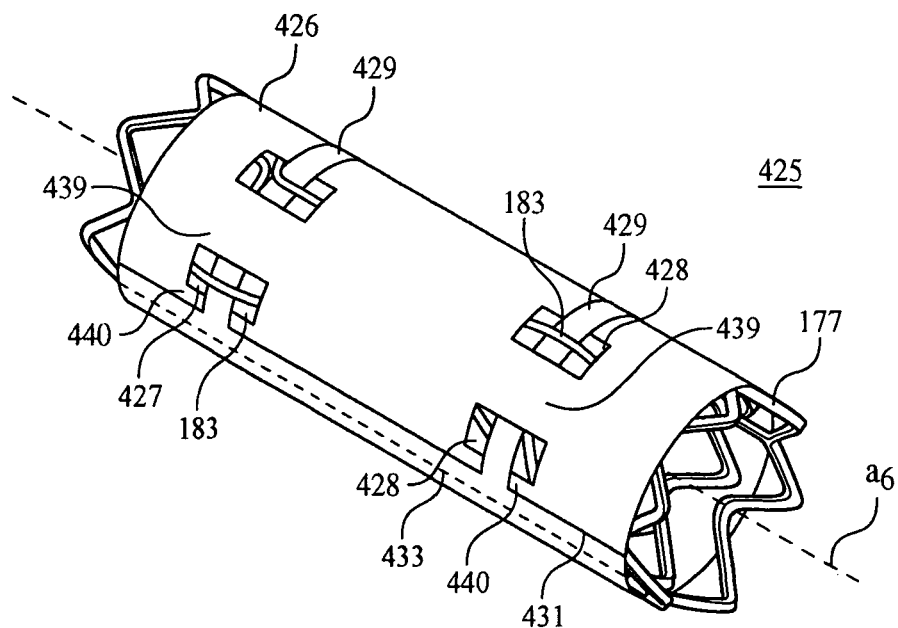
FIG. 7a is a perspective view of an embodiment of an endoprosthesis including a stent body and a tubular member.

Referring to FIGS. 7a and 7b, an endoprosthesis 425 includes stent body 177 and a tubular member 426, which can be secured together with complementary elements that are integral with the stent body and tubular member. As seen in FIG. 7b, tubular member 426 includes elongate bands 429, which extend from an edge 431 of member 426. Elongate bands 429 extend at least partially around a circumference of prosthesis 425 and can extend beneath another portion of tubular member 426. Such engagement can maintain a desired three-dimensional structure, e.g., shape and diameter, of endoprosthesis 425. Alternatively, or in combination, elongate bands 429 can engage a longitudinal member 183 or other portion of stent body 177. Such engagement can limit or prevent relative radial and/or longitudinal movement of tubular member 426 and stent body 177.

As seen in FIG. 7a, elongate bands 429 extend through fenestrations 427, beneath a portion 439 of tubular member 426, and out of fenestrations 428. Elongate bands 429 also extend beneath longitudinal members 183 of stent body 177. Edge 431 can overlap at least a portion of tubular member 426 so that an opposing edge 433 is concealed. In other embodiments, opposed edge 433 overlaps edge 431. In such embodiments, elongate bands 429 can extend beneath a portion 440 of tubular member 426, out from fenestrations 427, over portion 439 and into fenestrations 428.

When tubular member 426 is configured in three dimensions, as shown in FIG. 7a, edge 431 is aligned generally with a longitudinal axis $a_6$ of prosthesis 425. In other embodiments, edge 431 extends at an angle to axis $a_6$. For example, edge 431 may spiral generally around a circumference of prosthesis 425.

Elongate bands 429 can have a longitudinal axis $a_7$. In some embodiments, axis $a_7$ and edge 431 are oriented generally perpendicular to one another. In other embodiments, axis $a_7$ is oriented at an angle of less than 90° with respect to edge 431. In some embodiments, axis $a_7$ and axis $a_6$ are oriented generally perpendicular to one another. In other embodiments, axis $a_7$ is oriented at an angle of less than 90° with respect to axis $a_6$. For example, one or both of elongate bands 429 may spiral generally around a circumference of prosthesis 425.

In some embodiments, tubular member 429 includes only 1 elongate band. In other embodiments, tubular member 426 includes at least 3, e.g., at least 4 elongate bands. The one or more elongate bands can be evenly spaced along a length of tubular member 426 or positioned at non-equal intervals. For example, one or more bands may be positioned near either or both of the proximal and distal ends of the prosthesis. One or more bands may be centrally located with respect to a length of the prosthesis.

Figure 8A:
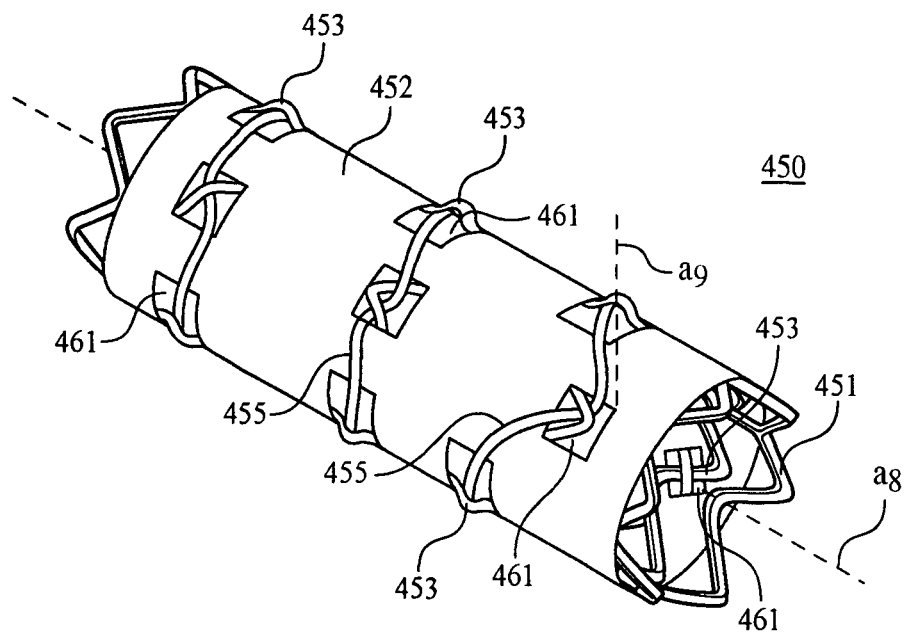
FIG. 8a is a perspective view of an embodiment of an endoprosthesis including a stent body and a tubular member.
Figure 8B:
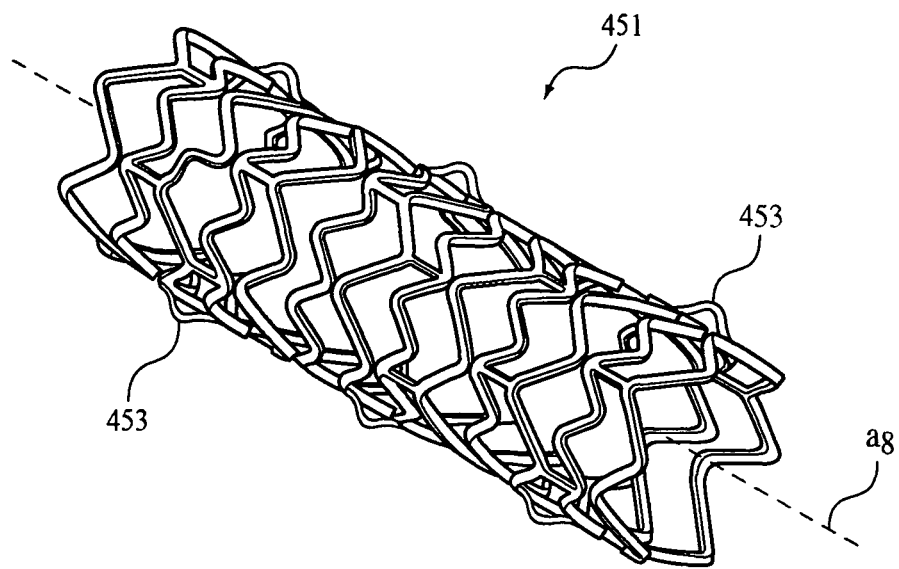

Referring to FIG. 8a, an endoprosthesis 450 includes a stent body 451 and a tubular member 452, which may include a thin film and other properties of tubular member 54. Referring also to FIG. 8b, stent body 451 includes a plurality of radial projections 453, which may be formed by bends or hooks in longitudinal members or connectors of the stent body. Projections 453 are shown as projecting outward from a radial center of prosthesis 450 but some or all of the projections may project inward. Projections 453 may be closed, e.g., as an eyelet or closed portion of the stent body or the projections may be open, as in a hook-shape. Tubular member 452 includes a plurality of fenestrations 461, each of which corresponds to a projection 453 of stent body 451.

Tubular member 452 circumferentially surrounds stent body 451 so that projections 453 are accessible via fenestrations 461. In some embodiments, at least a portion of projections 453 extends outward through fenestrations 461. Filaments 455 extend circumferentially around at least a portion of prosthesis 450. Filaments 455, fenestrations 461, and projections 453 cooperate to form a plurality of retention sites that limit or prevent relative movement between tubular member 452 and stent body 451. Filaments 455 are generally disposed adjacent an opposite surface of tubular member 452 from stent body 451. For example, if tubular member 452 surrounds stent body 451, filament 455 can be disposed adjacent an external surface of the tubular member.

In some embodiments, filaments 455 radially constrict tubular member 452 about stent body 451, such that tubular member 452 is compressed between the filaments and stent body 451. In other embodiments, filaments 455 provide essential no radial compression but limit a radial freedom of movement between tubular member 452 and stent body 451 such that they do not become substantially displaced along a longitudinal axis of the prosthesis.

Projections 453 define a longitudinal axis a9 extending therethrough. In some embodiments, all or some of projections 453 are oriented so that axes a9 are generally aligned with longitudinal axis a8 of prosthesis 450. In some embodiments, all or some of projections 453 are oriented so that axes a9 are generally perpendicular to axis a8. In some embodiments, filaments 455 extend longitudinally as opposed to or in combination with circumferentially extending filaments. Fenestrations and projections can be positioned at similar or different locations with respect to the length of prosthesis 450 as, e.g., retention sites of prostheses 100, 125, and 135.

Figure 8C:
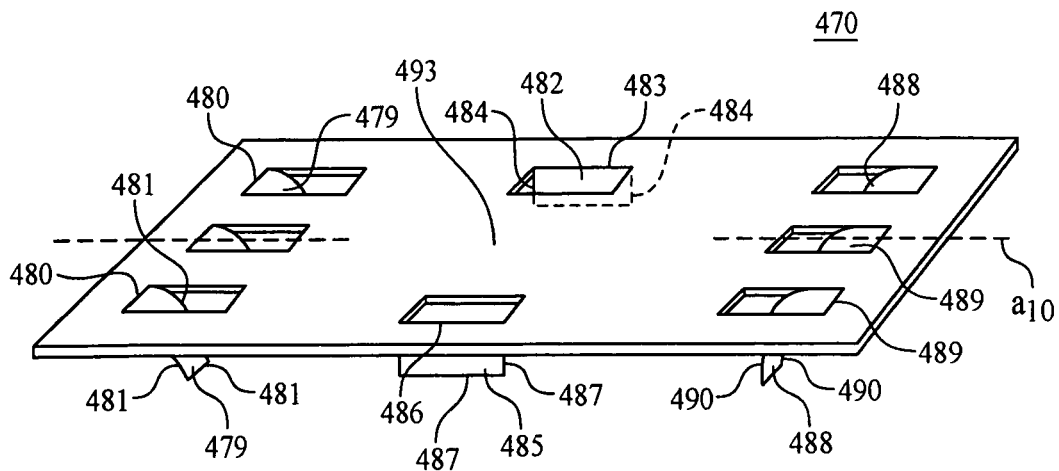
FIG. 8c is a perspective view of an alternative tubular member for use with the stent body of FIG. 8b. The tubular member is shown in two dimensions.

Referring to FIG. 8c, a tubular member 470 is configured for retention to a stent body, such as to stent body 451 having projections 453. Member 470 includes a plurality of projections 479, each defined by a fixed edge 480 and a plurality of free edges 481, a projection 482, defined by a fixed edge 483 and a plurality of free edges 484, a projection 485, defined by a fixed edge 486 and a plurality of free edges 487, and a plurality of projections 488, each defined by a fixed edge 489 and a plurality of free edges 490.

Although shown as two-dimensional, tubular member 470 can be manufactured in an initially three-dimensional state or made three-dimensional, e.g., by rolling member 470 about longitudinal axis a10 or about an axis oriented at an angle thereto, e.g., perpendicular thereto. Member 470 can be circumferentially mated with stent body 451 by positioning member 470 about the stent body. Projections of tubular member 470 engage projections 453 of the stent body to limit or reduce relative movement between member 470 and stent body 453.

In some embodiments, some or all of the projections of the tubular member 470 are oriented to engage projections 453 of stent body 451 having an axis a9 that is generally perpendicular to axis a8 of stent body 451. Such an engagement configuration can allow tubular member 470 and stent body 451 to have some circumferential freedom of movement while being more limiting with respect to longitudinal freedom of movement. In some embodiments, some or all of the projections of the tubular member 470 are oriented to engage projections 453 of stent body 451 having an axis a9 that is generally aligned with axis a8 of stent body 451. Such an engagement configuration can allow tubular member 470 and stent body 451 to have some longitudinal freedom of movement while being more limiting with respect to circumferential freedom of movement.

In some embodiments, some or all of the projections are oriented so that a fixed edge of the projection is generally perpendicular to a longitudinal axis of the stent body. For example, fixed-edge 480 of projection 479 and fixed edge 489 of projection 488 would each be perpendicular to axis a8 of stent body 451 if the tubular member were rolled about axis a10 and mated with the stent body. In some embodiments, some or all of the projections are oriented so that a fixed edge of the projection is generally aligned with a longitudinal axis of the stent body. For example, fixed edge 483 of projection 482 and fixed edge 486 of projection 485 would be aligned with axis a8 of stent body 451 if the tubular member were rolled about axis a10 thereof.

Projections 479, 482, 485, and 488 are shown as projecting toward an interior 493 of tubular member 470. In some embodiments, some or all of the projections project toward an outer edge of the tubular member.

Figure 9:
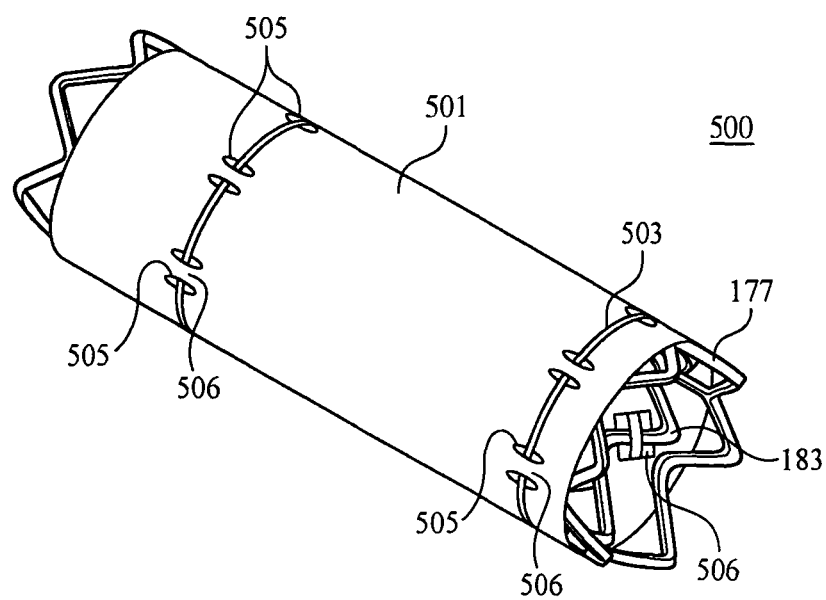
FIG. 9 is a perspective view of an embodiment of an endoprosthesis including a stent body and a tubular member.

Referring to FIG. 9, a prosthesis 500 includes a tubular member 501 and a stent body 177 secured by filament 503. Tubular member 501 includes fenestrations 505, which are defined by slits or cut-outs. Filament 503 passes through a fenestration 505 and beneath a portion 506 of tubular member 501, where the filament engages stent body 177, e.g., a longitudinal member 183. Filament 503 passes back to the exterior of tubular member 501 through another fenestration 505.

Figure 10A:
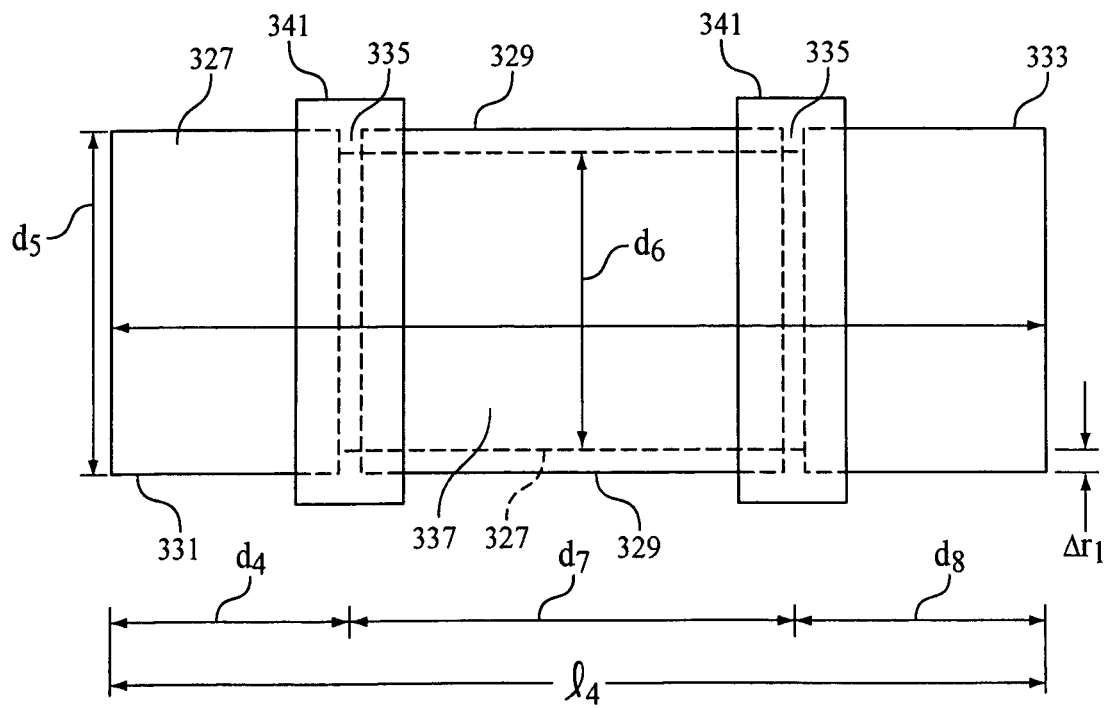
FIG. 10a is an embodiment of an endoprosthesis including a stent body and a tubular member.
Figure 10B:
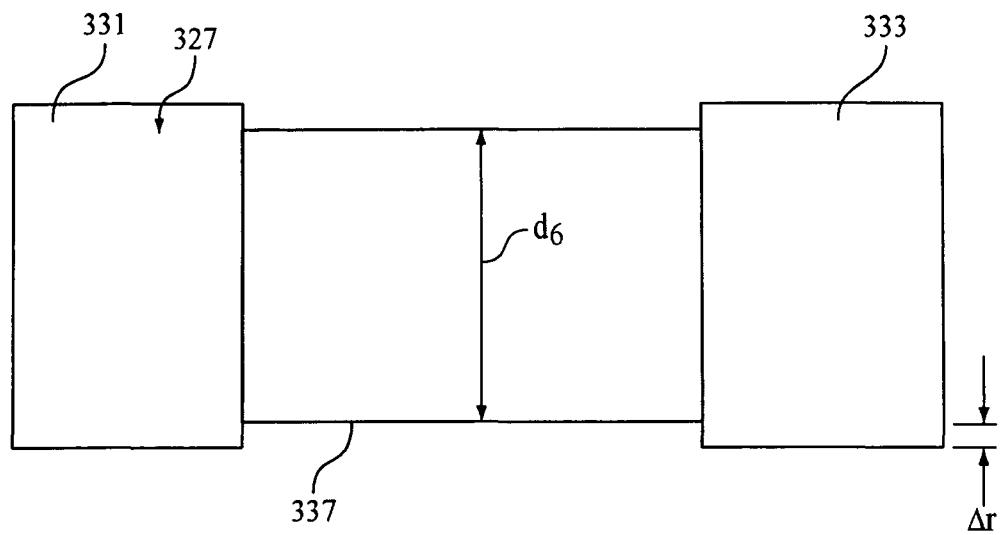
FIG. 10b is a side view of the stent body of FIG. 10b.
Figure 10C:
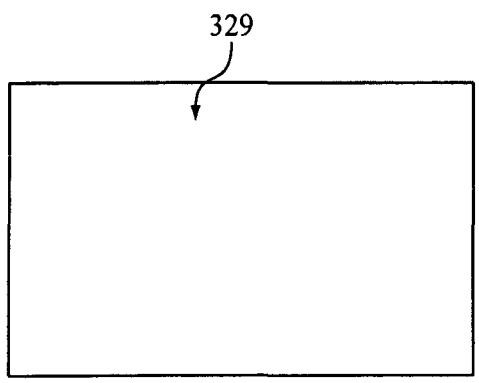

Referring to FIGS. 10a-10c, an endoprosthesis 325 includes a stent body 327 and a tubular member 329, which may include a film or thin film structure as described for tubular member 54. Stent body 327 includes a portion 331 having a diameter d5 and a portion 337 having a smaller diameter d6. At least a portion of tubular body 329 occupies a recess that results from the difference in radii between portions 331,337. A radial differential $\Delta r_1$ may provide the recess with a depth sufficient to fully accommodate tubular member 329 with respect to a radial direction. In some embodiments, radial differential $\Delta r_1$ is at least 7.5 µm, at least 15 µm, or at least 25 µm. In some embodiments, radial differential $\Delta r_1$ is 250 µm or less, 125 µm or less, 75 µm or less, 50 µm or less, e.g., 25 µm or less. A difference $\Delta d$ in diameter between portions 331,337 is given by $2\Delta r_1$.

In some embodiments, tubular member 329 has a smaller expanded diameter than portion 337 of stent body 327 would have in the absence of member 329. Hence, portion 337 of stent body 327 may exert a radial force against tubular member 329 in the radially expanded state of the prosthesis 325.

In some embodiments, portion 337 is formed by radially removing material from the stent body. For example, material may be removed from the stent body chemically, as by etching, or mechanically, as by grinding. In some embodiments, portion 337 is formed by adding additional material to portion 331. For example, diameter d5 can be increased by sputtering material, e.g., nitinol, onto portion 331.

Portion 331 may be located at either a distal end or a proximal end of prosthesis 325. Portion 331 extends a distance d4 along a length l4 of prosthesis 325. Portion 337 extends a distance d7 along length l4. A ratio of d4 to 14 may be at least 0.05, at least 0.1, e.g., at least 0.2. A ratio of d4 to 14 may be 0.3 or less, 0.2 or less, 0.15 or less, e.g., 0.1 or less. A ratio of d7 to 14 may be at least 0.5, at least 0.6, at least 0.8, at least 0.9 or at least 0.95. Various dimensions for prosthesis 325 are with reference to the radially expanded state of the prosthesis.

In some embodiments, prosthesis includes a second portion 333, which has a larger diameter than portion 337. In general, portion 333 has a diameter identical to portion 331. Portion 333 extends a distance d8 along length 14 of prosthesis 325. A ratio of d8 to 14 may assume values as described for the ratio of d4 to 14.

In some embodiments, a gap 335 is present between portion 331 and 337. Gap 335 may have a width sufficient to accommodate differential expansion between the stent body and tubular member. A ratio of a total width of gaps 335 to length l4 may be 0.25 or less, 0.15 or less, 0.075 or less, e.g., 0.05 or less.

In some embodiments, portion 331 and optional portion 333 exert a higher radial force than portion 337. For example, a radial outward force exerted by portions 331,333 may be at least 20%, at least 50%, or at least 100% greater than a radial outward force exerted by portion 337.

Stent body 327 and tubular member 329 can be secured using any of the retention techniques discussed herein, e.g., mechanically, by welding, by brazing, or adhesively. In some embodiments, stent body 327 and tubular member 329 are secured radially but are allowed some longitudinal freedom of movement along length 14 so as to accommodate length changes during expansion and contraction. An exemplary embodiment includes at least one circumferential collar 341, which is secured to either the stent body or tubular member 329 but generally not to both. Collar 341 may be formed of a metal, e.g., a superelastic alloy, or polymer. Collar 341 may be secured using, e.g., mechanical, welding, brazing, or adhesive techniques. In some embodiments collar 341 allows tubular member at least radial freedom of movement. For example, radial differential $\Delta r_1$ may exceed a diameter of tubular member 329, which may have an expanded diameter intermediate diameter d5 and d6.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application No. 11/025,464, titled MEDICAL DEVICES INCLUDING METALLIC FILMS AND METHODS FOR MAKING SAME, and filed concurrently herewith, which application is incorporated herein by reference.

An endoprosthesis may include features to enhance a flexibility of the endoprosthesis as described in U.S. patent application Ser. No. 11/025,158, titled MEDICAL DEVICES INCLUDING METALLIC FILMS AND METHODS FOR MAKING SAME, and filed concurrently herewith, which application is incorporated herein by reference.

An endoprosthesis may include a deposited thin film and a polymer as described in U.S. patent application No. 11/025,867, titled MEDICAL DEVICES INCLUDING METALLIC FILMS AND METHODS FOR MAKING SAME, and filed concurrently herewith, which application is incorporated herein by reference.

An endoprosthesis may include one or more filaments, e.g., wires, adapted to enhance mechanical properties of a deposited thin film as described in U.S. patent application No. 11/025,684, titled MEDICAL DEVICES INCLUDING METALLIC FILMS AND METHODS FOR MAKING SAME, and filed concurrently herewith, which application is incorporated herein by reference.

Methods for loading an endoprosthesis into a delivery device and systems for delivering an endoprosthesis to a treatment site are described in U.S. patent application No. 11/025,660, titled MEDICAL DEVICES INCLUDING METALLIC FILMS AND METHODS FOR LOADING AND DEPLOYING SAME, which application is incorporated herein by reference.

All publications, references, applications, and patents referred to herein are incorporated by reference in their entirety.

Other embodiments are within the claims.

What is claimed is:

1. An endoprosthesis for deployment within a body passage, comprising:
   a framework having a plurality of projecting eyelets disposed along a length of the framework;
   a tubular member comprising a metallic film having a thickness of about 50 μm or less and being generally coextensive with at least a portion of the framework, the tubular member having a plurality of fenestrations such that each eyelet passes through a different fenestration; and
   a plurality of circumferential filaments, wherein a circumferential filament passes through a plurality of eyelets around a circumference of the framework to retain the framework and the tubular member with respect to one another.

2. An endoprosthesis for deployment within a body passage, comprising:
   a framework having a plurality of projections disposed along a length of the framework, wherein each of the projections has a first end and second fixed end disposed on the surface of the framework;
   a tubular member comprising a metallic film having a thickness of about 50 μm or less and being generally coextensive with at least a portion of the framework, the tubular member having a plurality of fenestrations such that the each of the plurality of projections passes through a different fenestration; and
   a plurality of circumferential filaments, wherein a circumferential filament passes through the first and second fixed ends of a plurality of projections around a circumference of the framework to retain the framework and the tubular member with respect to one another, wherein each of the projections has a first and second fixed end, and wherein the at least one filament extends between the first and second fixed ends.

* * * * *